US010012613B2

(12) United States Patent
Minerick et al.

(10) Patent No.: US 10,012,613 B2
(45) Date of Patent: Jul. 3, 2018

(54) METHODS AND SYSTEMS FOR IDENTIFYING A PARTICLE USING DIELECTROPHORESIS

(71) Applicant: MICHIGAN TECHNOLOGICAL UNIVERSITY, Houghton, MI (US)

(72) Inventors: Adrienne Robyn Minerick, Houghton, MI (US); Jeana L. Collins, Houghton, MI (US); Kaela M. Leonard, Braintree, MA (US); Tayloria N.G. Adams, Chassell, MI (US)

(73) Assignee: Michigan Technological University, Houghton, MI (US)

(*) Notice: Subject to any disclaimer, the term of this patent is extended or adjusted under 35 U.S.C. 154(b) by 59 days.

(21) Appl. No.: 15/027,014

(22) PCT Filed: Oct. 6, 2014

(86) PCT No.: PCT/US2014/059332
§ 371 (c)(1),
(2) Date: Apr. 4, 2016

(87) PCT Pub. No.: WO2015/051372
PCT Pub. Date: Apr. 9, 2015

(65) Prior Publication Data
US 2016/0238558 A1 Aug. 18, 2016

Related U.S. Application Data

(60) Provisional application No. 61/887,178, filed on Oct. 4, 2013.

(51) Int. Cl.
*G01N 27/447* (2006.01)
*G01N 15/10* (2006.01)
(Continued)

(52) U.S. Cl.
CPC ....... *G01N 27/44791* (2013.01); *B03C 5/005* (2013.01); *G01N 15/1031* (2013.01);
(Continued)

(58) Field of Classification Search
CPC ....... G01N 27/44791; G01N 33/49707; G01N 15/1031; G01N 2015/0073; G01N 2015/1006; B03C 5/005
See application file for complete search history.

(56) References Cited

U.S. PATENT DOCUMENTS

| 5,122,805 A | 6/1992 | Peterman et al. |
| 2004/0112748 A1 | 6/2004 | Lee et al. |

(Continued)

FOREIGN PATENT DOCUMENTS

WO 98/04355 2/1998

OTHER PUBLICATIONS

PCT/US2014/059332 International Search Report and Written Opinion dated Jan. 15, 2015 (11 pages).
(Continued)

*Primary Examiner* — J. Christopher Ball
(74) *Attorney, Agent, or Firm* — Michael Best & Friedrich LLP

(57) ABSTRACT

A system for identifying a particle. The system includes a microfluidic device; a microelectrode array including a plurality of electrodes, the microelectrode array disposed within the microfluidic device; a plurality of particles suspended in a solution and delivered to the microelectrode array using the microfluidic device; a signal generator operatively coupled to the microelectrode array; a particle detector adjacent to the microelectrode array; and a controller in operative communication with the signal generator and the particle detector. The controller is configured to apply an oscillating voltage signal to the microelectrode array
(Continued)

between a low frequency and a high frequency at a sweep rate, wherein the sweep rate is no more than a maximum sweep rate, and determine a distribution of the plurality of particles relative to the microelectrode array at a plurality of frequency levels between the low frequency and the high frequency.

12 Claims, 27 Drawing Sheets

(51) Int. Cl.
    B03C 5/00        (2006.01)
    G01N 33/487     (2006.01)
    G01N 15/00      (2006.01)

(52) U.S. Cl.
    CPC ............... *G01N 33/48707* (2013.01); *G01N 2015/0073* (2013.01); *G01N 2015/1006* (2013.01)

(56) References Cited

U.S. PATENT DOCUMENTS

| | | |
|---|---|---|
| 2006/0254920 A1 | 11/2006 | Gascoyne et al. |
| 2009/0229980 A1 | 9/2009 | Hughes et al. |
| 2010/0203580 A1 | 8/2010 | Bryning et al. |
| 2012/0142032 A1 | 6/2012 | Morgan et al. |
| 2013/0118903 A1 | 5/2013 | Becker et al. |
| 2013/0192958 A1 | 8/2013 | Ding et al. |

OTHER PUBLICATIONS

PCT/US2014/059332 International Preliminary Report on Patenetability and Written Opinion dated Apr. 5, 2016 (2 pages).
A. Salmanzadeh et al., "Dielectrophoretic differentiation of mouse ovarian surface epithelial cells, macrophages and fibroblasts using contactless dielectrophoresis," article, Biomicrofluidics, 6, 13 pages (2012).
A. Salmanzadeh et al., "Lab on a Chip—Isolation of prostate tamer initiating cells (TICs) through their dielectrophoretic signature," article, 12, pp. 182-189 (2012).
C. Grosse et al., Corrigendum to "Dielectric dispersion in aqueous colloidal systems," article, Current Opinion in Colloid & Interface Sciences 18, 145 pp. 161-163 (2010).
C. Zhang et al., "Dielectrophoresis for manipulation of micro/nano particles in microfluidic systems," article, Analytical and Bioanalytical Chemistry, 396, pp. 401-420 (2010).
C.P. Jen et al., "A handheld preconcentrator for the rapid collection of cancerous cells using dielectrophoreses generated by circular microelectrodes in stepping electric fields," article, Biomicrofluidics 5, pp. 1-10 (2011).
Voskaridou et al., "Sickle-cell disease and the heart: review of the current literature," article, British Journal of Haematology, 157, pp. 664-673 (2012).
F. Groin et al., "Accumulation and trapping of hepatitis A virus particles by electrohydrodynamic flow and dielectrophoresis," article, Electrophoresis 27, pp. 1386-1393 (2006).
G.H. Markx et al., "Apparatus for separating by dielectrophoresis WO1994022583 A1," article, pp. 1-17 (1994).
G.M. Lock, "Manipulation of particles in liquid media," article, 11 pages (2001).
H. Morgan et al., "Interfacial polarisation and the effective dipole of particles," Journal Title—AC Electrokinetics: colloids and nanoparticles, Michigan Technological University Document, 12 pages (2003).
H. Park et al., "Dielectrophoresis force spectroscopy for colloidal clusters," article, Electrophoresis 33, pp. 2491-2497 (2012).
H. Xie et al., "Development of a 3D Graphene Electrode Dielectrophoretic Device," article, Journal of Visualized Experiments, 88, e51696, pp. 1-11 (2014).
H. Zhao, "Double-layer polarization of a non-conducting particle in an alternating current field wit applications to dielectrophoresis," article, Electrophoresis 32, 2232-2244 (2011).
H. J. Kim et al., "Microfluidic deice to separate micro-beads with various fluorescence intensities," article, Sensors and Actuators B-Chemical, 160, 1536-1543 (2011).
J. Ford, "Red blood cell morphology," article, International Journal of Laboratory Hematology, 35, 351-357 (2013).
J. Yang et al., "Differential Analysis of Human Leukocytes by Dielectrophoretic Field-Flow-Fractionation," article, Gascoyne, Biophysical Journal, 78, 2680-2689 (2000).
K. Khoshmanesh et al., "Dielectrophoretic platforms for bio-microfluidic systems," article, Biosensors & Bioelectronics 26, 1800-1814 (2011).
K. Ogata, "Transient Response Specifications," Journal Title—System Dynamics, Michigan Technological University Document, Chapter 8, Sec. 8-5, 3 pages (1978).
K.M. Leonard et al., "Explorations of ABO-Rh antigen expressions on erythrocyte dielectrophoresis: Changes in cross-over frequency," article, Electrophoresis 32, pp. 2512-2522 (2011).
L. Rozitsky et al., "Quantifying continuous-flow dielectrophoretic trapping of cells and micro-articles on microelectrode array," article, Biomed Microdevices 15, pp. 859-856 (2013).
L.A. Flanagan et al., "Unique Dielectric Properties Distinguish Stem Cells and Their Differentiated Progeny," article, Stem Cells 26, pp. 656-665 (2008).
M. Cristofanilli et al., "Dielectric cell separation of fine needle aspirates from tumor xenografts," article, Journal of Separation Science 31, pp. 3732-3739 (2008).
M. Mittal et al., "Polarization and interactions of colloidal particles in ac electric fields," article, Journal of Chemical Physics 129, pp. 065413-1 to 065413-7 (2008).
M. Carcao, The diagnosis and Management of Congenital Hemophilia, article, Seminars in Thrombosis and Hemostasis 38, pp. 727-734 (2012).
O.G. Martinsen et al., "Interface Phenomena and Dielectric Properties of Biological Tissue," article Encylcopedia of Surface and Colloid Science, pp. 2643-2652 (2002).
P. Gascoyne et al., "Microfluidic Approaches to Malaria Detection," article, Acta Tropica 89, pp. 357-369 (2004).
R. An et al., "Solution pH change in ono-uniform alternating current electric fields at frequencies above the electrode charging frequency," article, Biomicrofluidics 8, pp. 064126-2 to 064126-13 (2014).
R. Holzel, "Dielectric and dielectrophoretic properties of DNA," article, Iet Nanobiotechnology, vol. 3, issue 2, pp. 28-45 (2009).
R. Pethig et al., "Dielectrophoresis: A Review of Applications for Stem Cell Research," article, Journal of Biomedicine and Biotechnology, 182581 pp. 1-7 (2010).
R. Pethig et al., "Review Article—Dielectrophoresis: Status of the theory, technology, and applications," Biomicrofluidics 4, 35 pp. 022811-1 to 022811-35 (2010).
S.H. Liao et al., "Precisely sized separation of multiple particles based on the dielectrophoresis gradient in the z-direction," article, Microfluidics and Nanofluidics 12, 201-211 (2012).
S.K. Srivastava et al., "DC insulator dielectrophoretic applicatons in microdevice technology: a review," article, Analytical and Bioanalytical Chemistry 399, 301-321 (2011).
S.K. Srivastava et al., "Dielectrophoretic characterization of erythrocytes: Positive ABO blood types," article, Electrophoresis 29, 5033-5046 (2008).
T. Yasukawa et al., "Simple Detection of Surface Anigens on Living Cells by Applying Distinct Cell Positioning with Negative Dielectrophoresis," article, Analytical Chemistry 84, 8830-8836 (2012).
X.B. Wang et al., "Cell Separation by Dielectrophoretic Field-Flow-Fractionation," article, Analytical Chemistry 72, 832-839 (2000).

(56) References Cited

OTHER PUBLICATIONS

Z.G. Xiao et al., "Placement and Routing for Cross-Referencing Digital Microfluidic Biochips," article, IEEE Transactions on Computer-Aided Design of Integrated Circuits and Systems vol. 30, No. 7, pp. 1000-1010 (2011).

Z.R. Gagnon, Cellular Dielectrophoresis: Applications to the characterization, manipulation, separation and patterning of cells, article, Electrophoresis 32, 2466-2487 (2011).

EP148502073 Extended European Search Report dated May 23, 2017 (8 pages).

METHODS AND SYSTEMS FOR IDENTIFYING A PARTICLE USING DIELECTROPHORESIS

CROSS-REFERENCE TO RELATED APPLICATIONS

This application is a national stage filing under 35 U.S.C. § 371 of International Application No. PCT/US2014/059332 filed on Oct. 6, 2014, which claims priority to U.S. Provisional Patent Application No. 61/887,178 filed on Oct. 4, 2013, the entire contents of which are both incorporated herein by reference.

STATEMENT REGARDING FEDERALLY-SPONSORED RESEARCH OR DEVELOPMENT

The present invention was conceived while performing work under CBET 0644538, CBET 1041338, and IIP 1340126, each of which has been awarded by the National Science Foundation. The government has certain rights in the invention.

INTRODUCTION

The present invention relates to identification of particles based on dielectrophoretic responses.

SUMMARY OF THE INVENTION

In one embodiment, a system for identifying a particle includes a microfluidic device; a microelectrode array including a plurality of electrodes, the microelectrode array disposed within the microfluidic device; a plurality of particles suspended in a solution and delivered to the microelectrode array using the microfluidic device; a signal generator operatively coupled to the microelectrode array; a particle detector adjacent to the microelectrode array; and a controller in operative communication with the signal generator and the particle detector. The controller is configured to apply an oscillating voltage signal to the microelectrode array between a low frequency and a high frequency at a sweep rate, wherein the sweep rate is no more than a maximum sweep rate, and determine a distribution of the plurality of particles relative to the microelectrode array at a plurality of frequency levels between the low frequency and the high frequency.

In another embodiment, a method of identifying a particle. The method includes the steps of: placing a plurality of particles adjacent a microelectrode array, the microelectrode array including a plurality of electrodes; applying an oscillating voltage signal to the microelectrode array, the oscillating voltage signal varying between a low frequency and a high frequency at a sweep rate, wherein the sweep rate is no more than a maximum sweep rate; and determining a distribution of the plurality of particles relative to the microelectrode array at a plurality of frequency levels between the low frequency and the high frequency.

Other features and aspects of the invention will become apparent by consideration of the following detailed description and accompanying drawings.

DETAILED DESCRIPTION

Figure 1:
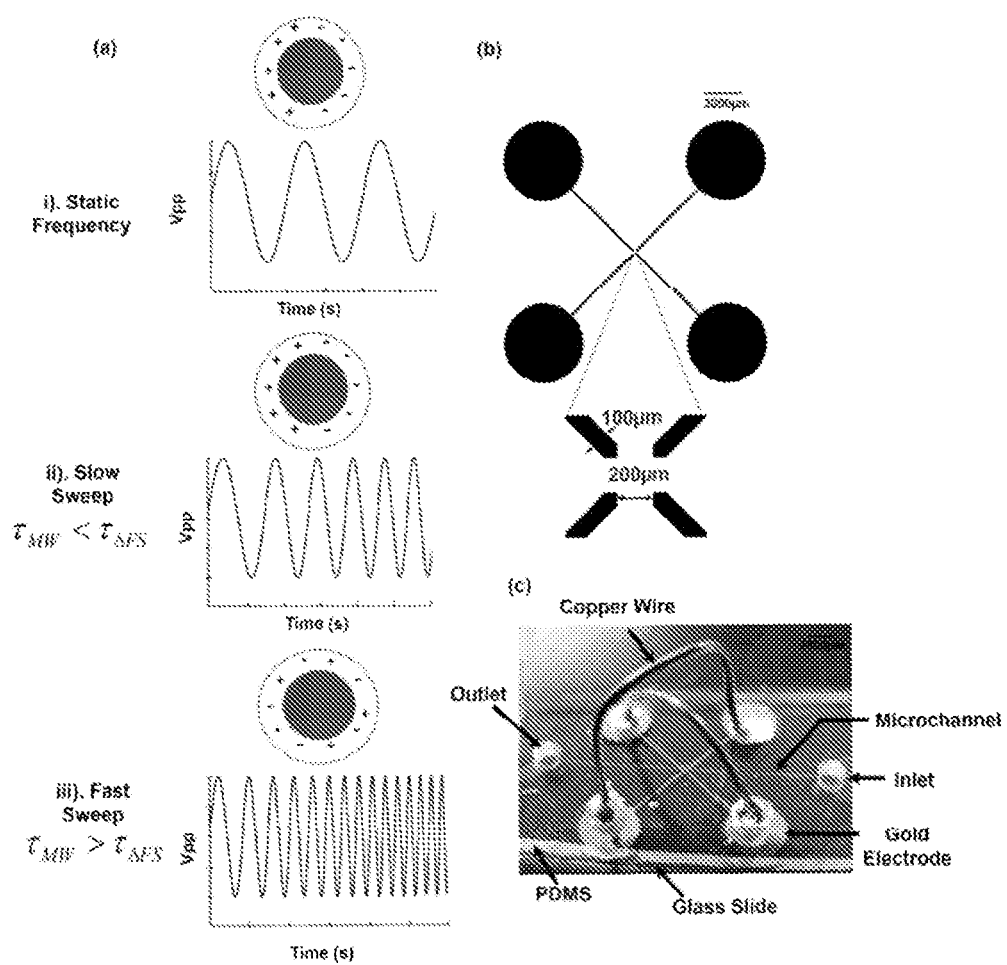
FIG. 1 shows (a) Dielectric relaxation mechanism for PS beads showing cases when i) particle polarization occurs at a static frequency, ii) $\tau_{MW}$ is shorter than the slow frequency sweep rate ($\tau\Delta_{FS}$) allowing the bead interface time to polarize in response to the non-uniform AC field, and iii) $\tau_{MW}$ is longer than the $\tau\Delta_{FS}$ for fast frequency sweep rates and the bead interface does not have time to fully polarize. (b) Schematic of the quadrapole electrodes micro patterned onto a glass slide, and (c) microdevice with PDMS fluidic layer bonded above the quadrapole electrodes silver-epoxied to copper leads.
Figure 2:
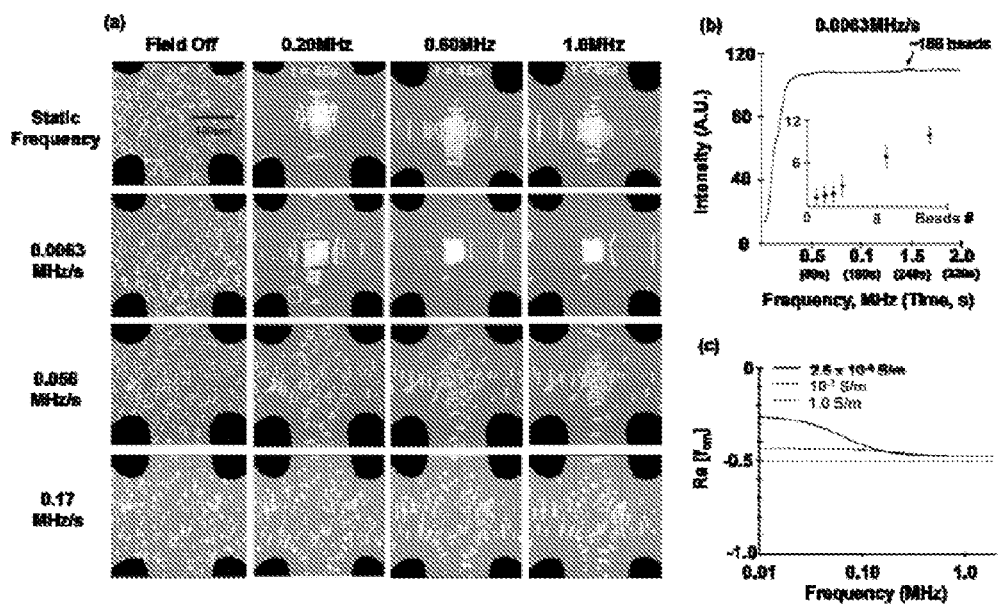
FIG. 2 shows (a) nDEP behavior of 6 µm PS beads suspended in E-pure $H_2O$ 2.5×10$^{-4}$ S/m and 250$V_{pp}$/cm 0.0063, 0.056 and 0.17 MHz/s sweep rates from 0.010 MHz to 1.0 MHz. (b) Raw intensity (arbitrary units) profile of PS beads in the center nDEP region (boxes shown at 0.20 MHz) at 0.0063 MHz/s sweep rate. Inset is a calibration of intensity per bead. (c) Clausius-Mossotti factor for the PS beads from 0.010 MHz to 2.0 MHz at three conductivities of 2.5×10$^{-4}$, 1.0×10$^{-3}$, and 1.0 S/m. PS bead assembly at slower frequency sweep rates track static frequency responses while 0.056 MHz/s illustrates transitional behavior and frequency sweeps above 0.17 MHz/s substantially lag the true static frequency DEP responses.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

Alternating current (AC) dielectrophoresis (DEP) experiments for biological particles in microdevices have typically been applied at fixed frequencies. Reconstructing the DEP response curve from static frequency experiments is laborious, but is important for ascertaining differences in dielectric properties of biological particles. The disclosed systems and methods, on the other hand, employ the novel concept of sweeping the frequency as a function of time to rapidly determine the DEP response curve from fewer experiments. Homogeneous 6.08 µm polystyrene (PS) beads were initially used as a model system to determine whether sweeping the frequency would be a viable method for generating DEP responses and then to identify an optimal sweep rate. Subsequent experiments were performed using the sweep rate approach with ~7 µm red blood cells (RBC) to verify that this approach would also work with biological samples. A Au/Ti quadrapole electrode microfluidic device was used to separately subject particles and cells to $10V_{pp}$ AC electric fields at frequencies ranging from 0.010-2.0 MHz over sweep rates from 0.00080 to 0.17 MHz/s. PS beads exhibited negative DEP assembly over the frequencies explored, likely due to Maxwell-Wagner interfacial polarizations. Results demonstrate that frequency sweep rates must be slower than particle polarization timescales; in some embodiments, sweep rates near 0.00080 MHz/s yielded DEP behaviors very consistent with static frequency DEP responses for both PS beads and RBCs, although higher sweep rates may also be employed.

Accordingly, disclosed herein are systems and methods for identifying a particle using dielectrophoresis (DEP). Embodiments of the methods and systems disclosed herein may be used to distinguish between different types of particles based on differences in dielectric properties of the particles. In various embodiments, the particles that are analyzed may include polystyrene beads (e.g. for testing purposes) or cells such as blood cells; in particular, different subtypes of red blood cells (e.g. A+, A−, O+, O−, etc.) may be distinguished based on the surface charge differences of the red blood cell subtypes (e.g. due to differing antigens on the cell surfaces). In general, the particles may range in size from about 1-50 µm and should be detectable (e.g. through optical or electrical means) using the particle detector (e.g. an imaging system).

A system according to embodiments of the invention may include a microfluidic device (which in some embodiments may include an enclosed microfluidic chamber) having a microelectrode array disposed in the fluid path of the microfluidic device. In various embodiments, particles are delivered to the vicinity of the microelectrode array using the microfluidic device prior to data collection. In certain embodiments, data collection is performed in a "batch-wise" manner, i.e. a group of particles is delivered to the microelectrode array and fluid movement is then stopped before data collection begins so that particle movements that are observed are due to dielectrophoresis.

Figure 5:
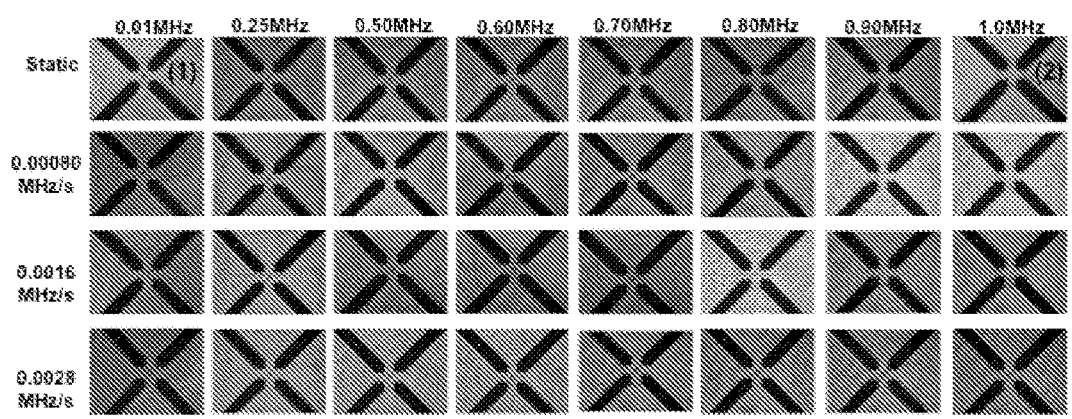
FIG. 5 shows an image comparison of the nDEP and pDEP behavior of A+ red blood cells suspended in 0.10 S/m dextrose solution and 1000$V_{pp}$/cm at 0.00080, 0.0016, and 0.0028 MHz/s sweep rates from 0.010 MHz to 1.0 MHz. (1) Denotes red blood cells nDEP behavior and (2) denotes red blood cell pDEP behavior. The red blood cells' DEP behavior at slower frequency sweep rates correlates well with the static frequency response (top row).

The microelectrode array in one embodiment is a quadrapole arrangement as shown, for example, in FIGS. 1, 2, 4, and 5. In this arrangement four electrodes are arranged in an "X" with a gap in the center (FIG. 5). Other possible arrangements of electrodes include interdigitated electrodes, V-shaped electrodes, circular electrodes, and T-shaped electrodes. In various embodiments, the electrodes are arranged so that oppositely charged electrodes are not parallel to one another, as this would create uniform fields whereas other, non-parallel geometries create non-uniform electric fields. In general, the electrodes are arranged so that they create a spatially non-uniform field. The electrodes are attached to the bottom of the microfluidic device and the particles that are delivered to the device are initially distributed in the vicinity of the electrodes in a random arrangement (e.g. see upper left panel of FIG. 2a) before any electrical signal is applied. The microelectrode array may be made by depositing metal strips onto a glass slide with a cover having a microfluidic channel being bonded on top of the glass slide (FIG. 1c). As shown in FIG. 1c, opposing pairs of electrodes may be electrically coupled using copper wires, as shown, with the leads (i.e. ground and "hot" AC signal) of a signal generator being connected to the copper wires. In various embodiments, pairs of electrodes may be electrically coupled as shown in FIG. 1c so that, upon stimulation, each electrode is 90° out of phase from the others to create a traveling wave signal.

Once particles have been delivered to the microelectrode array, a signal generator is used to deliver an oscillating voltage to the electrodes. In various embodiments, the voltage is applied at a peak-to-peak amplitude of $0.1V_{pp}$, $1V_{pp}$, $10V_{pp}$, $100V_{pp}$, or other suitable amplitude. In various embodiments, the oscillating voltage is applied at frequencies of at least about 0.001 MHz, at least about 0.005 MHz, at least about 0.01 MHz, at least about 0.05 MHz, at least about 0.1 MHz, at least about 0.5 MHz, or at least about 1.0 MHz. In other embodiments, the oscillating voltage is applied at frequencies of no more than about 10.0 MHz, no more than about 5.0 MHz, no more than about 2.0 MHz, no more than about 1.0 MHz, or no more than about 0.5 MHz.

In particular embodiments, the frequency of the oscillating voltage is varied, for example from a low frequency to a high frequency, in order to collect data at a variety of different frequencies, a process referred to as "sweeping" the frequency. In various embodiments, comparable results are obtained when the frequency is swept from a high frequency to a low frequency. Sweeping the oscillating voltage using a continuously varying frequency permits a relatively large amount of data to be gathered in a short period of time. The rate at which the frequency sweep, i.e. the "sweep rate," may vary from 0.00001 MHz/s to 0.1 MHz/s. In certain embodiments, the continuously varying frequency may be approximated by a series of discrete, step-wise changes in frequency with an increment ranging from about 10 nHz to about 10 Hz. As discussed herein, the optimum sweep rate may depend on conditions such as the conductivity of the solution in which the particles are suspended. The present inventors have found that when the frequency is swept above a certain maximum sweep rate the frequency changes too quickly, such that the particles do not have sufficient time to respond to the voltage signal at a given frequency before the signal changes to the next frequency. If the oscillating voltage signal is varied too quickly, i.e. above the maximum sweep rate, the observed particle movements and distributions will be inaccurate and could lead to an inconclusive or erroneous particle identification. Thus, in certain embodiments the maximum sweep rate is no more than about 0.003 MHz/s, no more than about 0.0029 MHz/s, no more than about 0.0028 MHz/s, no more than about 0.0027 MHz/s, no more than about 0.0026 MHz/s, no more than about 0.0025 MHz/s, no more than about 0.0020 MHz/s, no more than about 0.0015 MHz/s, no more than about 0.0010 MHz/s, no more than about 0.0008 MHz/s, or no more than about 0.0005 MHz/s. In various embodiments, a minimum sweep rate of at least about 0.00005 MHz/s, at least about 0.0001 MHz/s, at least about 0.00015 MHz/s, at least about 0.0002 MHz/s, at least about 0.0004 MHz/s, at least about 0.0005 MHz/s, at least about 0.00075 MHz/s, or at least about 0.0010 MHz/s may be used.

While the oscillating voltage is being applied to the microelectrode array at varying frequencies, data may be collected to determine the spatial distribution of the particles within the microfluidic device, particularly the particles in the vicinity of the electrodes, as a function of time. Particle detection may be carried out with systems which are capable of identifying the spatial distributions of the particles with sufficient temporal (e.g. operating at 0.1-10 Hz) and spatial (e.g. capable of resolving 0.1 µm×0.1 µm areas) resolution.

In some embodiments, images are collected at regular intervals (e.g. at video rates of 30 frames/sec or at other, slower rates such as 1 image or frame/sec) while sweeping the oscillating voltage. The images may be processed (for example several sequential video-rate frames may be averaged together) and the images or subregions thereof may be analyzed to characterize particle distribution and behavior at one or several frequencies. The analyses may include one or more of determining the particles' intensity profiles, transient responses, and velocities. Analyses may be conducted at one or more discrete locations within the images including along one or more lines, e.g. lines running between electrode tips. Analysis patterns for a sample which includes an unknown particle may be compared to patterns generated under equivalent conditions using known particles to determine the identity of the unknown particle. In certain embodiments in which only a few (e.g. 2-3) types of particles need to be distinguished, it may be sufficient to analyze only two subregions of the particle distribution in order to reliable distinguish the particle types from one another. In other embodiments in which a larger number of particle types are possible it may be necessary to analyze more subregions in order to reliably distinguish among particle types. For example, in order to distinguish among the eight red blood cell subtypes (A+, A−, B+, B−, O+, O−, AB+, and AB−) it may be necessary to analyze at least 4 different subregions of the particle distribution, and greater accuracy would be achieved by including more of the particle distribution in the analysis. In general, regions and patterns on the substrate are selected for analysis based on the areas that are expected to have the greatest change in electric field patterns and hence the greatest change in particle distribution at different frequencies, so as to provide the most information for distinguishing between particle types. Additional methods for analyzing DEP behavior of particles are disclosed in Salmanzadeh et al. (2012), Rozitsky et al. (2013), and An et al. (2014), each of which is incorporated herein by reference.

A system for carrying out embodiments of the invention may include a controller for carrying out one or more of the procedures disclosed herein. The controller may be in operative communication with one or more of the signal generator (which in turn is in communication with the microelectrode array) and the particle detector (e.g. imaging system). The controller may be a part of or in communication with a computer system. The computer system may be part of an existing computer system (e.g. on a smartphone, desktop computer, on-board computer, etc.) or may be implemented as a separate, standalone unit that is in local or remote communication with other components. The computer system(s) may be in wired or wireless communication with other systems through a combination of local and global networks including the Internet. Each computer system may include one or more input device, output device, storage medium, and processor (e.g. a microprocessor). Input devices may include a microphone, a keyboard, a computer mouse, a touch pad, a touch screen, a digital tablet, a track ball, and the like. Output devices include a cathode-ray tube (CRT) computer monitor, an LCD or LED computer monitor, touch screen, speaker, and the like.

The computer system may be organized into various modules including an acquisition module and an output module along with the controller, where the controller is in communication with the acquisition module and the output module. The various modules for acquiring and processing data and for returning a result may be implemented by a single computer system or the modules may be implemented by several computer systems which are in either local or remote communication with one another.

Storage media include various types of local or remote memory devices such as a hard disk, RAM, flash memory, and other magnetic, optical, physical, or electronic memory devices. The processor may be any known computer processor for performing calculations and directing other functions for performing input, output, calculation, and display of data in accordance with the disclosed methods. In various embodiments, implementation of the disclosed invention includes generating sets of instructions and data that are stored on one or more of the storage media and operated on by a controller, where the controller may be configured to implement various embodiments of the disclosed invention.

Some embodiments the system may be in the form of a portable or handheld device which may be self-contained, including the microfluidic device, microelectrode array, the controller, and additional components such as a power supply and input/output capabilities.

Without being limited as to theory, DEP enables phenotypically similar biological cells to be discriminated based on dielectric properties including the conductivity and permittivity of the membrane, cytoplasm, and other structurally relevant organelles. Cell components and structure contribute to a cell's signature dielectric dispersion. A particle's complex permittivity is frequency dependent and characterized by dielectric dispersion regions (γ, β, and α, where $w_\alpha < w_\beta < w_\gamma$) specific to an applied frequency. Certain embodiments of this work to illustrate sweep rates uses frequencies in the range of 0.010 to 2.0 MHz in the β-dispersion region because the Clausius-Mossotti factor, which governs sign and polarization strength, for polystyrene beads is nearly constant over this range. Maxwell-Wagner theory describes the polarization mechanism of particles in the β-dispersion region as interfacial polarization where moving charges build around the interface of a charged or charge-neutral particle and exchange ions with the suspending medium. Interfacial particle polarization creates an induced dipole moment such that the particle experiences disproportionate forces in each half cycle of the alternating current (AC) field resulting in net particle movement.

Polarized particles can exhibit either positive dielectrophoresis (pDEP) or negative dielectrophoresis (nDEP) as a consequence of the frequency-dependent polarizability of the particle in the surrounding medium. Particles that exhibit pDEP move to high electric field regions and particles that exhibit nDEP move to low electric field regions. This motion up and down electric field gradients is described by the Clausius-Mossotti factor for spherical particles.

$$f_{cm} = \frac{\tilde{\varepsilon}_p - \tilde{\varepsilon}_m}{\tilde{\varepsilon}_p + 2\tilde{\varepsilon}_m},$$

$$\tilde{\varepsilon}_i = \varepsilon_i + \frac{\sigma_i}{\omega j},$$

where $\tilde{\varepsilon}_i$ is the complex permittivity of the particle (i=p) and of the medium (i=m), which are both functions of conductivity ($\sigma$), permittivity ($\varepsilon$), and angular frequency ($\omega$).

Polarization is not an instantaneous event; charge transport into the interface takes a few microseconds in response to the electric field. Maxwell-Wagner dielectric relaxation is a physical phenomenon related to the transport delay of cation and anion alignment in and around the interface of the dielectric particle. At lower frequencies (<~10 MHz), particle polarization is driven by this conductive polarization. At higher AC frequencies, charges do not have enough time to move into and around the interface double layer, so particles experience polarization lag time as a result of the rapidly modulating field and do not reach maximum polarization.

Maxwell-Wagner dielectric relaxation is characterized by a time constant, $\tau_{MW}$, which is unique to each particle or cell due to the time constant's dependence on the cell dielectric properties. The time required for a particle to reach maximum polarization is given by Eq. (3) (see Morgan et al. (2003), p. 27; see also Grosse et al. (2010) and Mittal et al. (2008), each of which is incorporated herein by reference):

$$\tau_{TW} = \frac{(\varepsilon_p + 2\varepsilon_m)\varepsilon_0}{\sigma_p + 2\sigma_m}.$$

Typical relaxation times for particle polarization vary from pico- to microseconds (see Morgan et al. (2003), p. 27; see also Grosse et al. (2010) and Mittal et al. (2008)), and the calculated $\tau_{MW}$ for polystyrene (PS) beads in our Epure $H_2O$ medium at $2.5\times10^{-4}$ S/m is 3.5 µs. Thus, a single AC cycle is on the order of 0.01 to 2 µs; the time delay in ion transport within a static frequency field of 0.010 to 2.0 MHz is such that 2 to 350 AC cycles must be completed before the particle experiences full polarization.

The Maxwell-Wagner dielectric timescale for charge transport into and around the interface becomes important when the frequency is swept, i.e. changes as a function of time. FIG. 1a highlights the Maxwell-Wagner particle polarization at the interface under static frequency as well as slow and fast frequency sweep rates. At a static frequency in the β-dispersion region, the particle experiences a constant frequency field such that the relaxation time is not a factor and the particle fully polarizes. A particle in a field with a slowly changing frequency sweep has a relaxation time, $\tau_{AFS}$, that is less than $\tau_{MW}$ and thus the particle interface fully polarizes. In contrast, a particle in a fast frequency sweep has a relaxation time, $\tau_{AFS}$, that is larger than $\tau_{MW}$ and the particle interface does not have time to fully polarize in the field. PS beads are lossy dielectric particles treated as homogeneous spheres and are thus an idealized particle to examine new techniques, devices, or approaches to dielectrophoretic characterizations. Our system is easily able to discern pDEP and nDEP transitional behavior and adaptable to new frequency sweep techniques. The homogeneous spherical DEP polarization model for PS beads ($\varepsilon$=2.5 and $\sigma$=9.4×10$^{-5}$ S/m) suspended in Epure $H_2O$ displays only nDEP behavior over 0.010 to 2.0 MHz.

Thus, microfluidic and dielectrophoretic (DEP) technologies enable a wide variety of particle polarizations with nonuniform electric fields on microchips to achieve particle manipulation, concentration, separations, and property-based identification. Particles can include bioparticles (e.g. DNA, viruses, or proteins) as well as cells (e.g. blood cells, cancer cells, stem cells, and yeast). The advantages to coupling DEP with microfluidics are small sample size (on the order of microliters), rapid analysis (approximately minutes to achieve results), minimal sample preparation, and minimal waste production. Traditionally, DEP experiments are completed at static, fixed frequencies such that maximum particle polarization can be achieved and measured. Multiple experiments are conducted, each at discrete frequencies over the range of interest to stitch together DEP response spectra; this is a labor-intensive approach. Further disadvantages are that extended field exposure times at fixed frequencies can change particle properties or cell viability. As disclosed herein, it is demonstrated that frequency can be swept with time in the β-dispersion region thus enabling interrogation of cells at multiple frequencies within a short time period. The benefits of using a frequency sweep technique are that nearly continuous DEP response curves, when coupled with automated response analysis, can be compiled in near real time and the number of experiments needed to obtain particle DEP spectra are greatly reduced.

Traditional DEP measurements are completed at single static frequencies in order to compile frequency by frequency, the DEP spectrum for a particle or cell system. This method is laborious and, as disclosed herein, requires time for particles to fully polarize for accurate observed DEP responses. The present disclosure describes the use of frequency sweeps as a means to more efficiently interrogate multiple frequencies in a single experimental run and systematically compared the responses to the nDEP response at fixed frequencies between 0.010 and 2.0 MHz. It was observed that frequency sweep rates influence the DEP response of PS beads and RBCs and further, the permissible frequency sweep rate is particle or cell dependent. The underlying mechanism appears to be the same. At slower sweep rates, particles have more time to polarize in the electric field and therefore a more accurate and reproducible DEP spectrum can be obtained. At faster frequency sweep rates, the particles are unable to achieve maximum interfacial polarization because of the dielectric relaxation time scale so the observed DEP response does not match the true DEP behavior of the particle.

For polystyrene beads at frequency sweep rates below 0.0063 MHz/s, responses correlate closely with dielectric responses of particles subjected to a static frequency potential. In the PS bead system, 0.056 MHz/s is the transitional sweep rate where the particle dielectric relaxation is approximately the same order of magnitude as the shifts in frequency within the sweep. Dielectric responses continue to track the static frequency responses, although reproducibility is diminished. However as this sweep rate is increased further, conductivity dominated interfacial polarizations cannot be established and the PS bead frequency sweep data does not coincide with static frequency measurements.

For full utility in DEP experiments, this frequency sweep rate methodology must be translatable to cell systems. Results illustrated that only 0.00080 MHz/s accurately predicted the static frequency DEP responses of human RBCs. Red blood cells are substantially more morphologically and dielectrically complex than polystyrene beads. Calculation of the dielectric relaxation time, taking into account only the membrane permittivity and conductivity of 4.4 and $10^{-7}$ S/m, respectively (Gascoyne et al. (2004), incorporated herein by reference) yields a dielectric relaxation time ~4.6 μs roughly corresponding to 0.21 MHz. This relaxation time is larger than the PS bead relaxation time of 3.5 μs, so the optimal frequency sweep rate for red blood cells would be slower than that for PS beads. This result suggests that for each new cell system of interest it is imperative to determine the optimal frequency sweep rate for accurately and reproducibly interrogating the behavior of that cell. This work outlines a systematic technique to make comparisons between frequency sweep rate and static frequency shown. For all cell systems, sweep rates that are too fast will not allow the cell adequate time to polarize and will result in inaccurate and less reproducible DEP responses. An optimal frequency sweep rate can be estimated by calculating the Maxwell-Wagner dielectric relaxation time for the particle/cell of interest, provided the cell's permittivity and conductivity is known. The frequency sweep rate chosen for the DEP study should then remain at frequencies below the inverse dielectric relaxation time ($1/\tau_{MW}$) for 5-45 s (longer times spent below the threshold give better DEP predictions).

Since the cell's permittivity and conductivity are determined from the frequency dependent DEP spectrum, this presents a cyclical situation. However, this work has demonstrated that frequency sweep rates slower than 0.00080 MHz/s can yield accurate DEP response of PS beads as well as RBCs. This sweep rate may therefore be translatable to other cell systems. In addition, at higher frequencies where the polarization mechanism is more heavily influenced by charge permittivity effects through the membrane and cell cytosol, it is possible that slow frequency sweep rates can still accurately capture DEP response spectra. Lastly, this frequency sweep rate technique will enable researchers to obtain accurate and continuous DEP response spectra in shorter experiment times.

The following non-limiting Examples are intended to be purely illustrative, and show specific experiments that were carried out in accordance with embodiments of the invention.

EXAMPLES

Example 1

In this Example, dielectrophoretic responses of PS beads (model system) were quantified at both static frequencies and frequency sweeps at rates ranging from 0.00080 to 0.17 MHz/s over the β-dispersion frequency range of 0.010-2.0 MHz. PS bead motion in the electric field was imaged with video microscopy and analyzed using three techniques: intensity profiles, transient response, and particle velocities. Data shows that frequency sweep rates impact particle polarization due to dielectric relaxation limitations. This frequency sweep technique was further extended in this Example to negatively charged biconcave red blood cells (RBCs), which are an important cellular system for medical disease diagnostics.

The microdevice shown in FIG. 1c was fabricated according to previously published microfabrication techniques (Grom et al. (2006), incorporated herein by reference), with the 100 μm wide electrodes spaced 200 μm apart aligned at 90° along the bottom of a 70 μm deep by 1000 μm wide microfluidic chamber as shown in FIG. 1b. Polystyrene beads (Cat No. PP-60-10, Spherotech, Lake Forest, Ill., USA), 6.08 μm in diameter were centrifuged at 1300 $\min^{-1}$ for 5 mins to separate the beads from the liquid. The PS beads were resuspended in Epure $H_2O$ (18 MΩ or $2.5 \times 10^{-4}$ S/m) at a 1:10 (bead to water) volumetric dilution ratio and vortexed. Microdevice was pre-rinsed with Epure $H_2O$ and Alconox precision cleaner (Cat No. 1104, Alconox Inc, White Plains, N.Y., USA) to prevent bead adhesion. PS bead-Epure $H_2O$ suspension was pumped to the microchamber using a syringe. Time was allowed for inlet and outlet pressures to equalize and flow to stop. The function generator (Agilent 33250A, Agilent, Santa Clara, Calif., USA) was connected via copper leads to produce a $10V_{pp}$ AC sine wave with frequencies ranging from 0.010-2.0 MHz at specific frequency sweep rates 0.00080, 0.0011, 0.0030, 0.0063, 0.013, 0.021, 0.028, 0.042, 0.056, 0.083, and 0.17 MHz/s. Frequency sweeps linearly increased the applied frequency as a function of time. Greater than five (n>5) static frequency experiments were completed at each frequency 0.010, 0.020, 0.030, 0.040, 0.050, 0.20, 0.40, 0.60, 0.80, 1.0, 1.2, 1.4, 1.6, 1.8, and 2.0 MHz by applying $10V_{pp}$ for 90 s. These DEP static frequency responses were compared to each frequency sweep rate DEP responses. For the static and frequency sweep experiments, the PS bead concentration was between 238-263 beads in the t=0 field of view. Video recordings of experiments were taken at 30 fps at 640×480 pixels/image using LabSmith SVM Synchronized Video Microscope with a 10× objective (LabSmith, Livermore, Calif., USA).

Video recordings of PS beads DEP behaviors were analyzed with ImageJ (NIH, Bethesda, Md.) using intensity, transient slope, and velocity measurements. Since PS beads only exhibit nDEP over the frequency range of interest, intensity data acquisition from images was completed by drawing a rectangular box at the device center, $I_{CTR}$, and background, $I_{BK}$ measured in a location with no PS beads present (See FIG. 2a). ImageJ Z Project function was used to average the pixel intensities in the specified boxed region. The initial background, $I_{BK}(t=0)$ and center intensity, $I_{CTR}(t=0)$ were subtracted from the center and background intensity at each time, $I_{CTR}(t)$ and $I_{BK}(t)$, and then a normalized intensity was calculated by dividing by the maximum intensity experienced by the PS beads, (Eq. (4)):

$$\bar{I}_{DEP,t} = \frac{[(I_{CTR} - I_{BK})_t + (I_{BK} - I_{CTR})_{t=0}]}{[(I_{CTR} - I_{BK})_t + (I_{BK} - I_{CTR})_{t=0}]_{MAX}}$$

This normalized intensity tracked the real-time magnitude of the PS bead DEP response, which had two distinct regions: transient where beads moved with nDEP toward the center, and steady-state (SS) where beads achieved tight packing at the device center. These two responses were analyzed separately via transient slope and particle velocity.

The transient response of the PS beads was extracted from the steady-state response via signal processing in which the delay and rise time were quantified. The PS bead delay time, $t_d$, was characterized as the time required for the intensity response to reach 50% of the final intensity response for the first time. The rise time, $t_r$, was determined as the time needed for the intensity response to reach 100% of the final intensity response for the first time (Ogata et al. (1978), pp. 517-518, incorporated herein by reference). This allowed the transient response to be segmented and a linear trend line was fit between $t_d$ and $t_r$, where $t_d < t_r$. A comparison of the transient slope for frequency sweep rates and static frequency measurements is given in FIG. 3c. PS bead velocities were determined from the original video by tracking the x-, y-pixel position of individual PS beads from 0-50 s. PS bead located within 5 μm of electrode tips were selected to control for similar electric field gradients. This procedure was repeated for at least 10 beads in each specific frequency sweep rate and static experimental video.

For experiments involving human RBCs, blood of the appropriate type (e.g. O+, A+, etc.) was obtained from a single donor and centrifuged at 1400 rpm for 5 mins to separate the packed RBCs from the plasma and leukocytes. The packed RBCs were removed, then resuspended at 1:75 v:v in 0.10 S/m isotonic dextrose buffer doped with 0.75% BSA (Cat No. A7906, Sigma Aldrich, St. Louis, Mo., USA) to prevent cell/device adhesion. This RBC suspension was syringe-pumped to the microchamber, with time being allowed for flow to stop after pumping before the $10V_{pp}$ signal was applied over 0.010-0.50 MHz (range reduced to avoid pDEP behavior) at frequency sweep rates of 0.00080, 0.0063 and 0.056 MHz/s (n=7). RBC static frequency experiments were completed at 0.010, 0.10, 0.25 and 0.50 MHz at $10V_{pp}$ for 90 s (n=7). Video microscopy at 25× and 1 fps was obtained with a Zeiss Axiovert Inverted Light Microscope (Zeiss, Germany). The video images were analyzed as described herein for the PS beads.

Frequency sweep rates ranging from 0.00080 to 0.17 MHz/s were explored to see if the nDEP response of PS beads would vary and/or correspond to static frequency measurements. The frequency range was chosen for the relatively consistent Clausius-Mossotti factor, $Re(f_{CM})$ for a homogeneous lossy polystyrene sphere of 0.26 to 0.48 (see FIG. 2c) over the frequency range of 0.010 to 2.0 MHz. Static frequency experiments were completed at fixed values in this same frequency range. FIG. 2a shows still images from both static frequency experiments and the frequency sweeps at 0.20, 0.60, and 1.0 MHz. For static frequencies, the response 45 seconds after field application is shown while for frequency sweeps of 0.0063, 0.056, and 0.17 MHz/s, the image is shown at the time stamp when the specified frequency is reached. The electrodes are visible as black shadows in the images and the PS beads assemble due to nDEP forces at the central electric field gradient minima Data was examined to determine the sweep rate that most closely approximated the static frequency response. Frequency sweeps 0.00080 and 0.0063 MHz/s (shown) tracked static frequency, or true, DEP responses while the slightly faster sweep of 0.056 MHz/s begins to lag the true DEP responses and at 0.17 MHz/s and faster, particles were unable to achieve sufficient polarization to respond sufficiently in the electric field.

nDEP responses were quantified via intensity analysis as described herein for all sweeps and all static frequency experiments. FIG. 2b illustrates the frequency- (and time-) dependent intensity for the 0.0063 MHz/s sweep rate images shown in FIG. 2a. This quantification of the PS bead nDEP response was correlated to total bead packing via the calibration shown in the inset. The 188-bead count at the center deviates slightly from the initial, field off, bead count of 245 because PS beads also move down the electric field gradient to regions outside of the image field of view.

Figure 3:
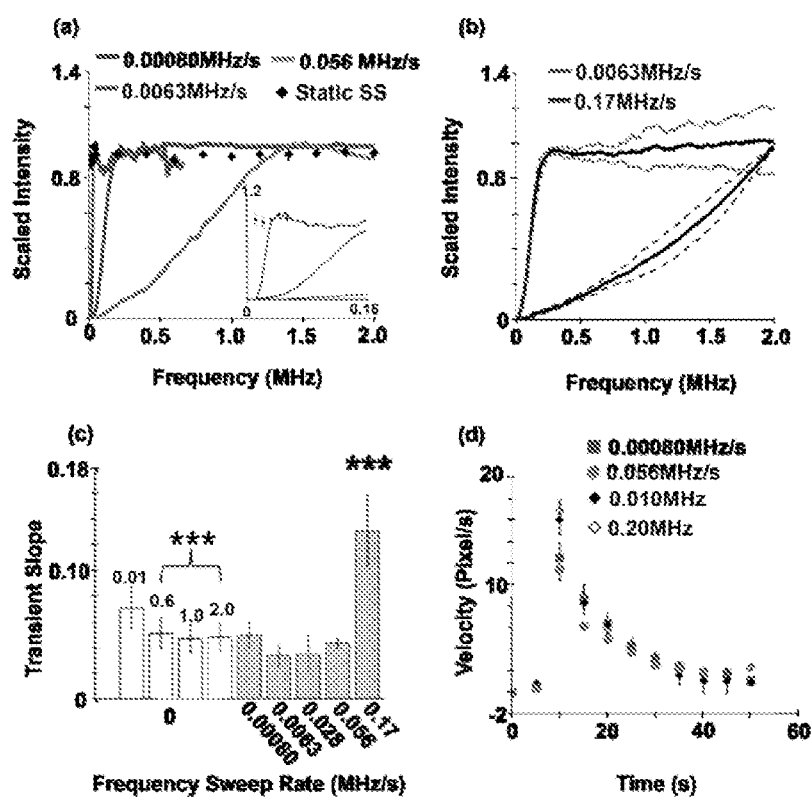
FIG. 3 shows (a) 6 µm PS beads nDEP intensity profiles for 0.00080, 0.0063, and 0.056 MHz/s and static steady state (SS) measurements (black diamonds). Intensity analysis captures bead assembly to the quadrapole center with transient and SS regions. The slowest frequency sweep rate of 0.00080 MHz/s best predicts the static DEP responses. (b) Bead assembly intensity (arbitrary units) profiles for 0.0063 (n=8) and 0.17 MHz/s (n=7) with 95% confidence upper and lower limits shown as dashed lines. (c) Transient slope comparison for static frequencies (0 MHz/s) as well as frequency sweeps. (d) Comparison of static frequency and frequency sweep PS bead velocities from 0 to 50 s. 0.00080 MHz/s results are consistently similar to the static frequency results.
Figure 4:
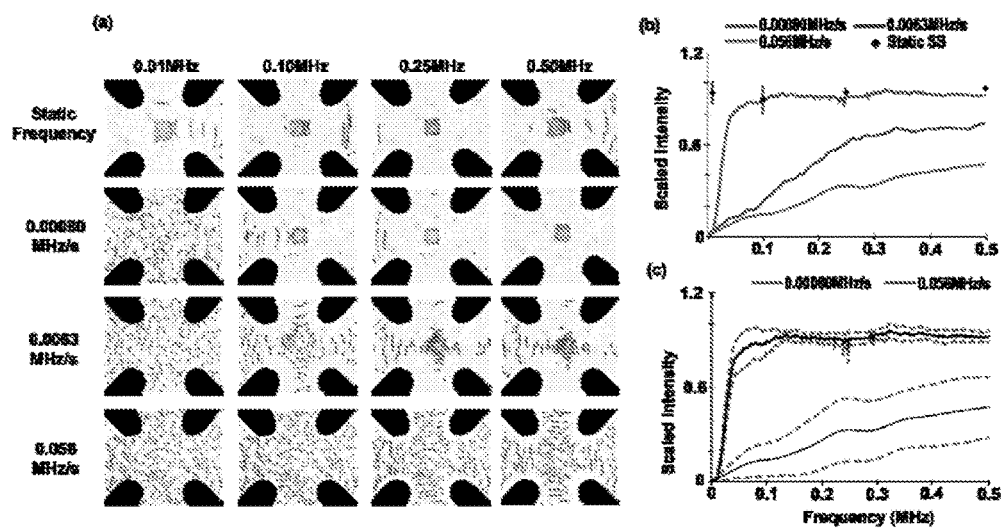
FIG. 4 shows (a) nDEP behavior of RBCs suspended in 0.1 S/m dextrose buffer and 250V/cm at 0.00080 MHz/s, 0.0063 MHz/s and 0.056 MHz/s sweep rates from 0.010 MHz to 0.50 MHz. (b) RBCs nDEP intensity (arbitrary units) profiles for 0.00080, 0.0063, and 0.056 MHz/s and static measurements. (c) 0.00080 and 0.056 MHz/s RBC assembly intensity (arbitrary units) profiles n=8, with 95% confidence interval upper and lower limits shown as dashed lines.

Normalized intensities, Eq. (4), were compiled in FIG. 3a for SS (i.e. 45 seconds) static frequency nDEP responses and 0.00080, 0.0063, 0.056 MHz/s frequency sweep rate nDEP responses. The time for sweep responses to achieve the true nDEP static response decreases as the sweep rate decreases. Frequency sweep rates 0.00080 and 0.0063 MHz/s are within the 95% confidence intervals (n=7) of the static steady-state (SS) responses. FIG. 3a inset shows that the slowest 0.00080 MHz/s sweep rate more quickly aligns closely with the static frequency responses. FIG. 3b compares average 0.0063 MHz/s (n=8) to 0.17 MHz/s (n=7) with the dashed lines signifying the upper and lower limits of the 95% confidence intervals for $I_{DEP}$. The confidence intervals around the transient 0.0063 MHz/s sweeps are smaller than for 0.17 MHz/s over much of the frequency range indicating greater reproducibility at slower sweep rates. Faster sweep rates either do not reach SS or have a lag before reaching SS (compare to FIG. 2a) suggesting the bead interface does not fully polarized and thus displays attenuated nDEP motion.

The transient behavior was quantified for all static frequencies and frequency sweeps via a transient slope analysis as compiled in FIG. 3c. Four static frequency measurements 0.010, 0.60, 1.0 and 2.0 MHz are shown compared to 0.00080, 0.0063, 0.028, 0.056, and 0.17 MHz/s frequency sweep rates. Static frequency transient slopes range between 0.023-0.095 and are within the 95% (p<0.05) confidence intervals of 0.00080, 0.0063, and 0.028 MHz/s frequency sweep transient slopes. These slower sweep rates and 0.056 MHz/s differ at p<0.001 from the fastest sweep rate of 0.17 MHz/s, which is also significantly different at p<0.001 from the static measurements (except for $1.0 \times 10^4$ Hz with p<0.01).

Individual bead velocities were compiled for static as well as frequency sweeps in FIG. 3d. PS bead velocity corroborates the intensity profile and the slope analysis that 0.00080 MHz/s frequency sweep rate closely tracks the bead velocity at static frequencies. 0.056 MHz/s gives good estimations of static frequency bead velocity at times greater than 20 s. Based on intensity, transient slope, and velocity analysis, the slow frequency sweep rate of 0.00080 MHz/s is most consistent with static frequency DEP responses.

There is an observable inverse relationship between the frequency sweep rate and particle polarization, where slower sweep rates result in comparable particle polarization characteristics to static frequency responses. Dielectric relaxation is the driving force of this relationship; the calculated dielectric relaxation time Eq. (3) for PS beads in E-pure $H_2O$ at $2.5 \times 10^{-4}$ S/m is 3.5 μs, which corresponds to ~0.28 MHz. There are two timescales that influence this behavior: the frequency itself and the change in frequency per time. The Maxwell-Wagner, conductivity-driven interfacial polarization mechanism occurs below ~0.28 MHz; above this frequency threshold the interfacial polarization of the PS beads gradually decreases and the particle permittivity increasingly influences the DEP force. The experimental frequencies tested were within the range dominated by Maxwell-Wagner polarization such that maximum particle interfacial polarization was possible.

The second timescale of interest is the frequency change per time or frequency sweep rate, which determines how many consecutive cycles a particle experiences a specific frequency. At slower sweep rates, the PS beads experience a specific frequency for a large number of cycles and thus the beads have time to polarize because the timescale of the frequency change is slower than the dielectric relaxation time. A particle must experience a single frequency during the sweep for a minimum of 3.5 µs for maximum interfacial polarization to be achieved. Upon polarization, the particle, which its current DEP force has to overcome inertia and Stokes drag to achieve observable particle motion down the electric field gradient. At static frequencies, it takes roughly 5 s for maximum velocity to be attained (see FIG. 3d, AC field applied at t=5 s) and as much as 45 s for final SS at the field gradient minima to be reached. As the sweep rate increases, the dielectric relaxation time and the rate of change of the frequency approach the same order of magnitude. Results suggest that 0.056 MHz/s is a transitional sweep rate because the DEP behavior roughly corresponds to the static behavior of the PS beads. With further increases in frequency sweep rates, the timescale for frequency change surpasses the dielectric relaxation timescale such that particles are unable to fully polarize resulting in an attenuated DEP response as shown with data in FIGS. 2, 3a, and 3b. FIG. 3b also demonstrates that the transient behavior of the PS beads is more reproducible at slower frequency sweep rates, which can be attributed to the interfacial polarization timescale of the beads. Implications of the intensity, slope, and velocity analysis compared with static frequencies are that slow frequency sweep rates accurately predict the DEP response of PS beads because the changes in frequency are slower than the characteristic Maxwell-Wagner dielectric relaxation.

Thus, a frequency sweep approach can be utilized to attain accurate DEP behavior of PS beads, provided the sweep rate is slower than conductivity mediated interfacial polarization timescale. This result is reliable over frequency ranges where particle polarization is dominated by the conduction of free charges from the media. The charges are moving around the PS beads through the particle-liquid interface inducing a dipole, which causes PS bead movement down the electric field gradient to the electrode center. At different sweep rates the rate of movement of the charges varies which varies the rate of the dipole being induced, observed as dielectric relaxation. Each sweep rate has a unique dielectric relaxation time and our results are consistent with Maxwell-Wagner interfacial polarization theory. 0.00080 MHz/s is the optimal sweep rate necessary to predict the true DEP behavior of PS beads because it allows for full or partial (when the frequency is above 0.28 MHz) polarization.

Given that the sweep methodology yielded accurate DEP responses for the ideal system of PS beads, the same methodology and frequency sweep rates were explored with human RBCs. The three most successful PS bead frequency sweep rates were reproduced with human red blood cells: 0.00080 MHz/s, 0.0063 MHz/s and 0.056 MHz/s. Static frequency experiments were also performed at 0.010 MHz, 0.10 MHz, 0.25 MHz and 0.50 MHz. Seen in FIG. 4a are 25× microscope images taken of the t=45 s final static frequency frames aligned above the sweep time points that correspond to those four static frequencies. Qualitatively, the only sweep rate that accurately matches the static frequency behavior of the human RBCs is 0.00080 MHz/s. This behavior was further verified by the same intensity analysis as for PS beads. In FIG. 4b, the scaled intensity is plotted for 0.00080, 0.0063 and 0.056 MHz/s experiments (n=8) as compared to the static frequency intensities. After the initial 10 s transition for the red blood cells to polarize and overcome drag, the slowest frequency sweep of 0.00080 MHz/s accurately predicts the static frequency behavior and is highly reproducible, with a very narrow 95% confidence interval range (FIG. 4c). The fastest sweep rate of 0.056 MHz/s does not predict the static behavior of the human RBCs and is much less reproducible, as evidenced by the large 95% confidence interval in FIG. 4c. From these experiments, we conclude that the optimal frequency sweep for determining the accurate DEP behavior of RBCs is 0.00080 MHz/s. Due to the complex dielectric properties of cells, it is necessary to carefully compare frequency sweep rates with static frequency behaviors to ascertain optimal frequency sweep rates that accurately interrogate the cell of interest.

Example 2

Figure 11:
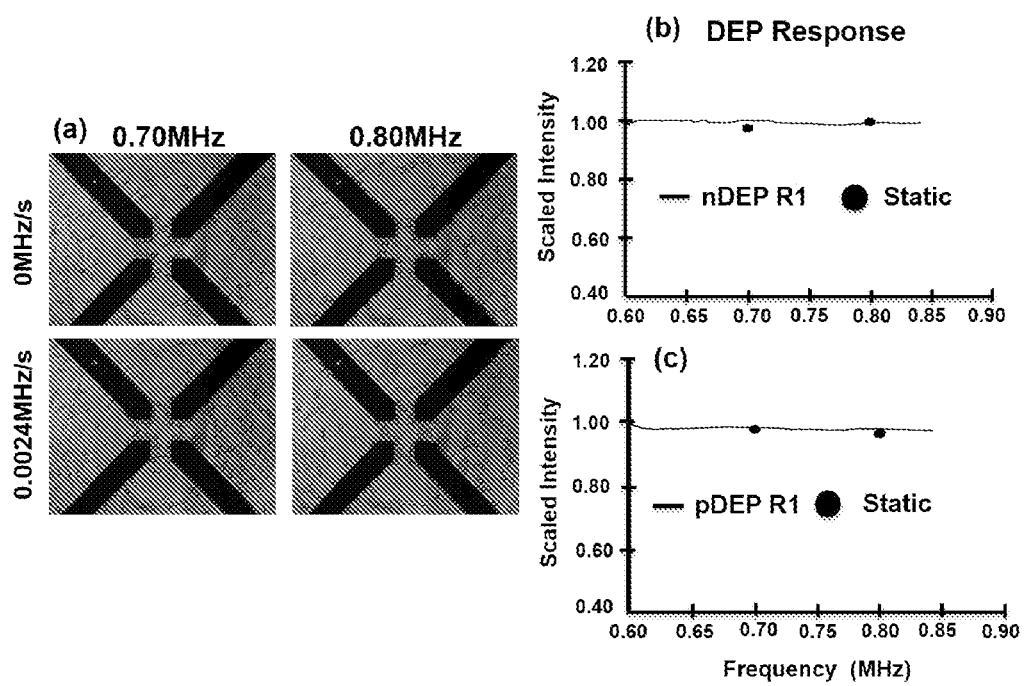
FIG. 11 illustrates (a) A− RBC static images (top row) compared to A− RBCs response using 0.0024 MHz/s (bottom row). (b) nDEP and (c) pDEP intensity profiles for 0.0024 MHz/s with RBC static steady state measurements (circles). The images and intensity profiles show good agreement with static measurements. Each test was completed in 0.10 S/m at $1000V_{pp}$/cm.
Figure 12:
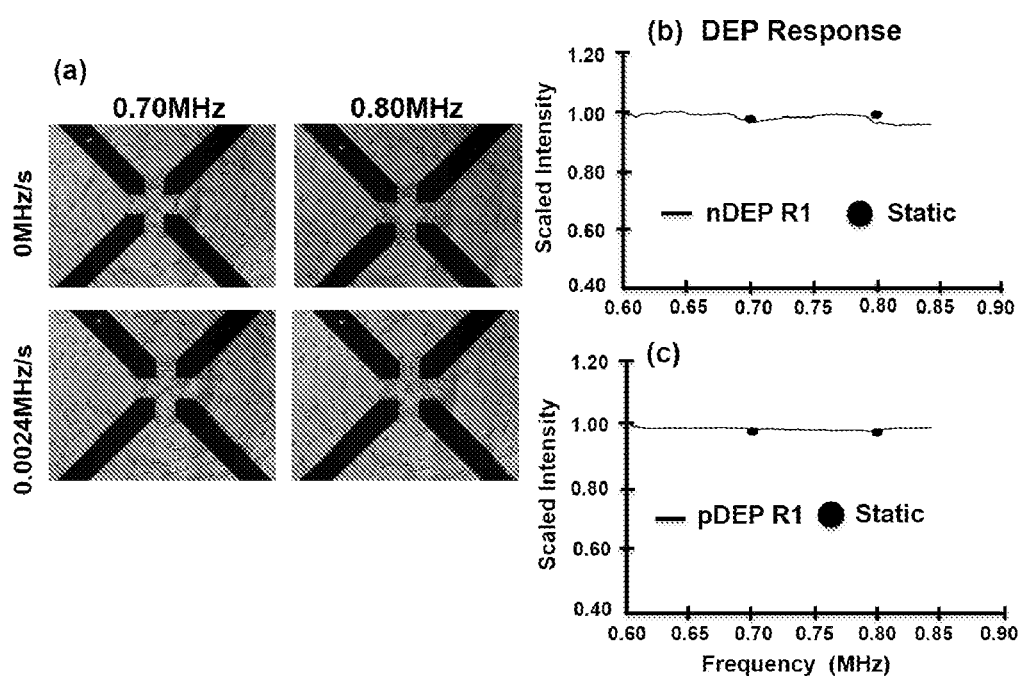
FIG. 12 illustrates (a) O+ RBC static images (top row) compared to O+ RBCs response using 0.0024 MHz/s (bottom row). (b) nDEP and (c) pDEP intensity profiles for 0.0024 MHz/s with RBC static steady state measurements (circles). The images and intensity profiles show good agreement at 0.70 MHz and fair agreement at 0.80 MHz. Each test was completed in 0.10 S/m at $1000V_{pp}$/cm.
Figure 13:
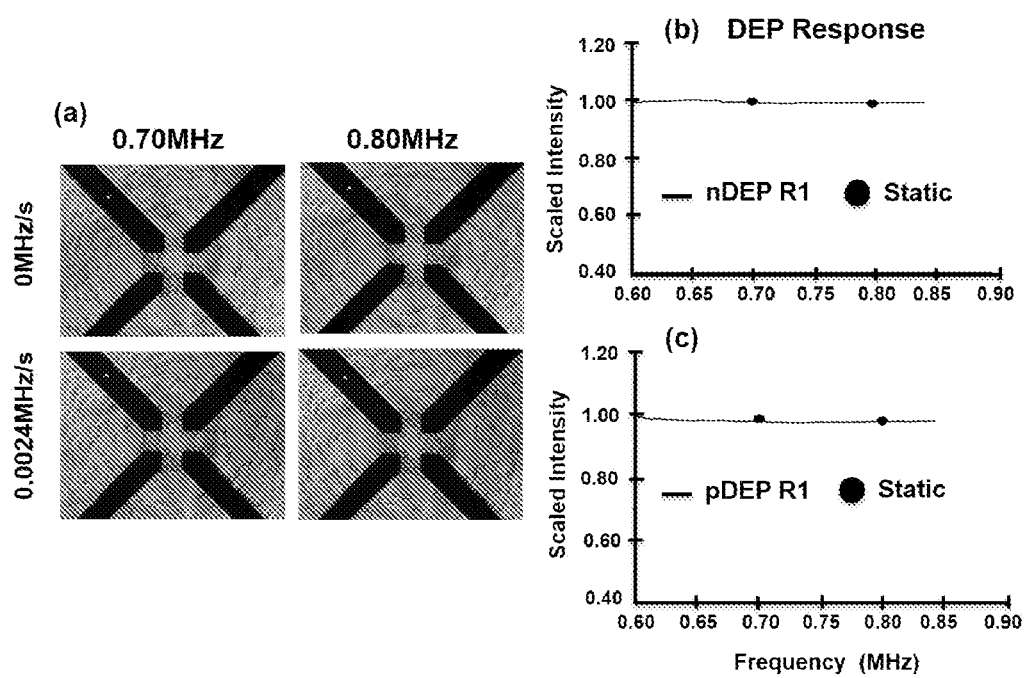
FIG. 13 illustrates (a) B+ RBC static images (top row) compared to OB+ RBCs response using 0.0024 MHz/s (bottom row). (b) nDEP and (c) pDEP intensity profiles for 0.0024 MHz/s with RBC static steady state measurements (circles). The images and intensity profiles show good agreement over the tested frequency range 0.60-0.84 MHz. Each test was completed in 0.10 S/m at $1000V_{pp}$/cm.

Conditions for Example 2 are the same as described above for Example 1 except where otherwise stated. FIGS. 5-13 show data obtained from applying a sweeping oscillating voltage signal of 1000 Vpp/cm to human red blood cells in a solution with conductivity of 0.10 S/m. FIGS. 5-10 show data obtained from A+ RBCs while FIG. 11 shows data from A− RBCs, FIG. 12 shows data from O+ RBCs, and FIG. 13 shows data from B+ RBCs.

Figure 6:
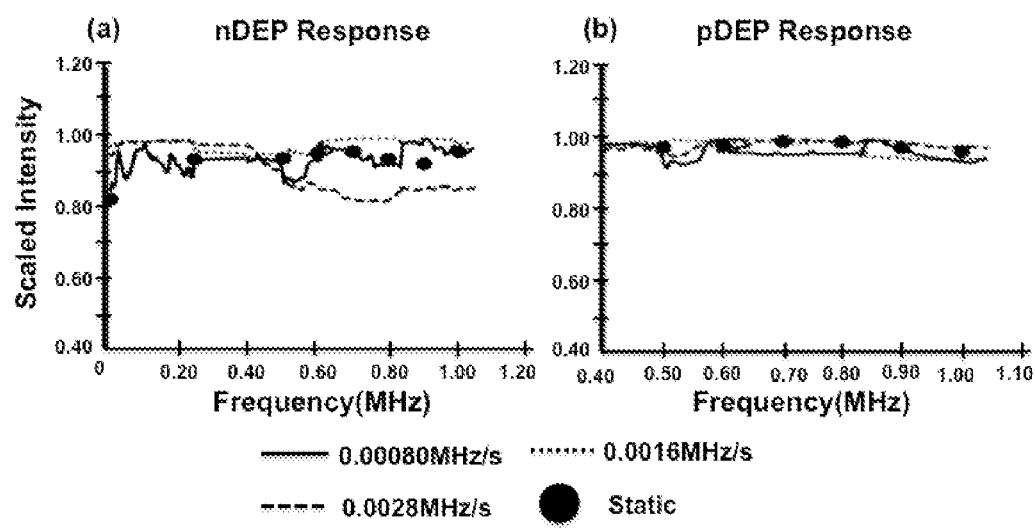
FIG. 6 illustrates (a) nDEP and (b) pDEP intensity profiles for 0.00080, 0.0016, and 0.0028 MHz/s and static steady state measurements (solid circle). The intensity (arbitrary units) analysis captures the RBCs assembly toward the electrode center (nDEP) and near the electrodes (pDEP). 0.00080 MHz/s is the slowest and 0.0016 MHz/s is the fastest sweep rate to best predict RBCs' static DEP response.
Figure 7:
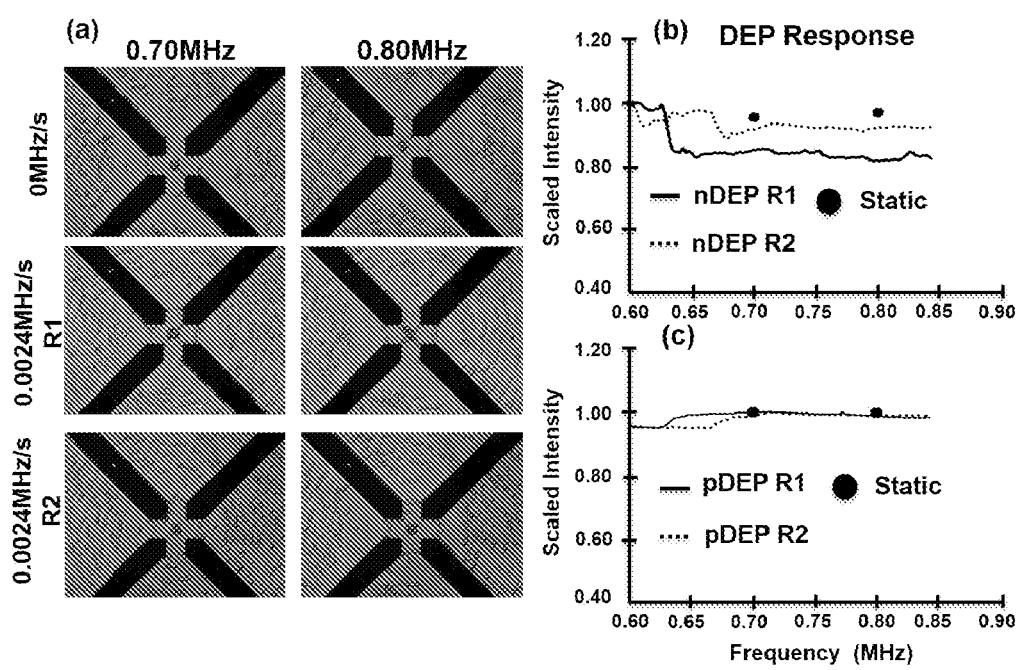
FIG. 7 illustrates (a) RBC static images (top row) compared to RBCs response using 0.0024 MHz/s (middle and bottom row). R1 and R2 are two different repeats completed for this measurement. (b) nDEP and (c) pDEP intensity (arbitrary units) profiles for 0.0024 MHz/s with RBC static steady state measurements (circles). The images and intensity profiles show the threshold frequency sweep rate at which agreement with static measurements is acceptable, but begins to falter. Sweep rates less than 0.0024 MHz/s agree well. Each test was completed with A+ blood in 0.10 S/m at $1000V_{pp}$/cm.
Figure 8:
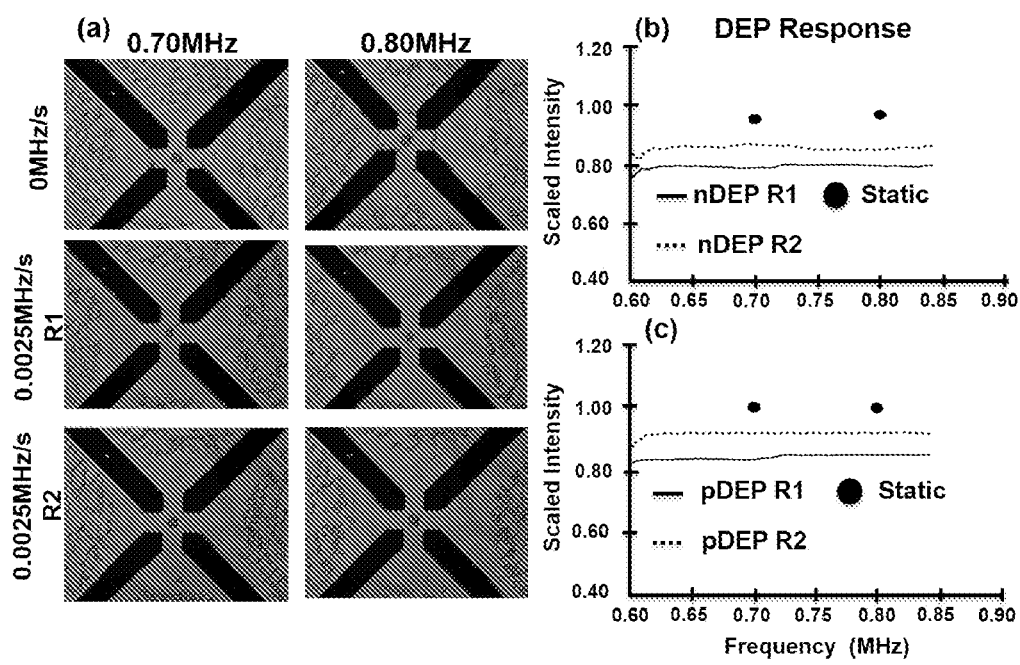
FIG. 8 illustrates (a) RBC static images (top row) compared to RBCs response using 0.0025 MHz/s (middle and bottom row). R1 and R2 are two different repeats completed for this measurement. (b) nDEP and (c) pDEP intensity profiles for 0.0025 MHz/s with RBC static steady state measurements (circles). The images and intensity profiles show poor agreement with static measurements. Each test was completed with A+ blood in 0.10 S/m at $1000V_{pp}$/cm.
Figure 9:
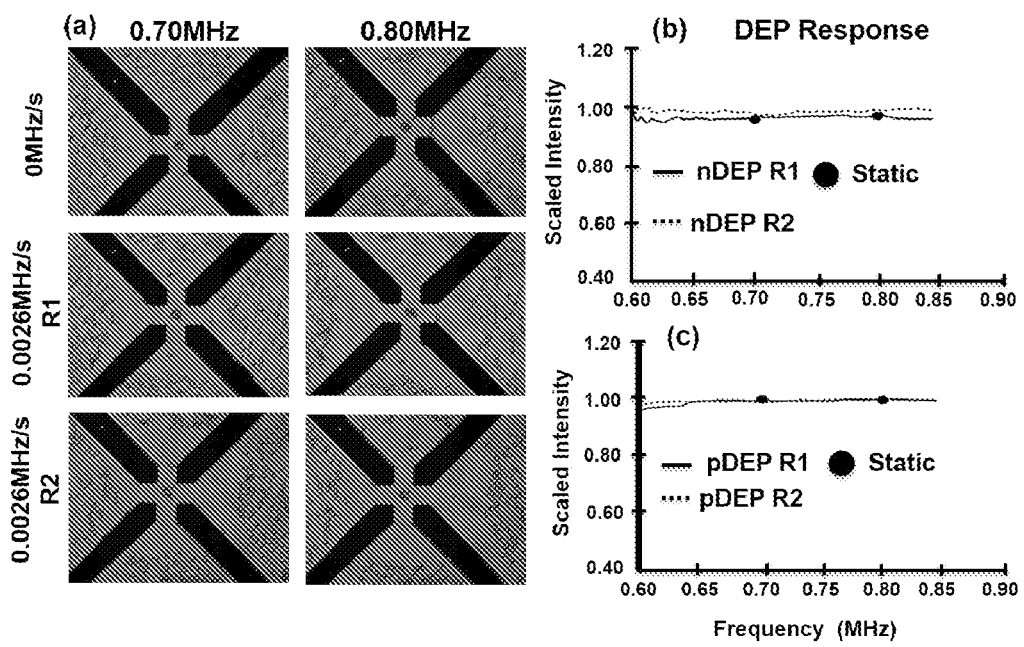
FIG. 9 illustrates (a) RBC static images (top row) compared to RBCs response using 0.0026 MHz/s (middle and bottom row). R1 and R2 are two different repeats completed for this measurement. (b) nDEP and (c) pDEP intensity profiles for 0.0026 MHz/s with RBC static steady state measurements (circles). The images show poor agreement and intensity profiles show good agreement with static measurements. Each test was completed with A+ blood in 0.10 S/m at $1000V_{pp}$/cm.
Figure 10:
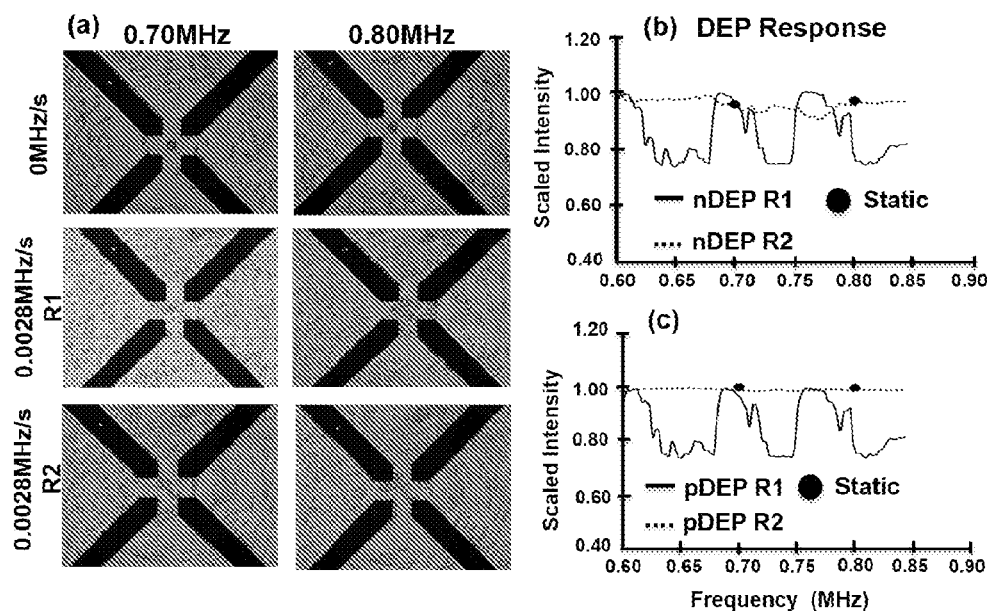
FIG. 10 illustrates (a) RBC static images (top row) compared to the response of RBCs using a sweep rate of 0.0028 MHz/s (middle and bottom row). R1 and R2 are two different repeats completed for this measurement. Panels (b) nDEP and (c) pDEP show intensity profiles for 0.0028 MHz/s with RBC static steady state measurements (circles). The images show poor agreement and intensity profiles illustrate the lack of reproducibility of agreement with static measurements. Each test was completed with A+ blood in 0.10 S/m at $1000V_{pp}$/cm.

FIG. 5 shows images of A+ RBCs distributed in the vicinity of quadrapole electrodes during application of an oscillating voltage having frequencies ranging from 0.01 MHz to 1.0 MHz applied statically or at sweep rates of 0.00080 MHz/s, 0.0016 MHz/s, or 0.0028 MHz/s. The notation "(1)" denotes RBCs demonstrating nDEP behavior and "(2)" denotes RBCs demonstrating pDEP behavior. The RBC's DEP behavior at slower frequency sweep rates (0.00080 MHz/s and 0.0016 MHz/s) correlates well with the static frequency response (top row), indicating that these are below the maximum sweep rate for these conditions. FIG. 6 compares the nDEP (panel (a)) and the nDEP (panel (b)) intensity profiles of the particles for the statically applied oscillating voltage as well as at the various sweep rates tested across the range of frequencies.

Panel (a) of each of FIGS. 7-13 shows images of particle distributions at oscillating voltages of 0.70 MHz and 0.80 MHz collected either with static application of the oscillating voltage ("0 MHz") or while sweeping at the indicated sweep rates. Panels (b) and (c) of each of FIGS. 7-13 show nDEP (panels (b)) and pDEP (panels (c)) intensity profiles throughout the frequency range relative to intensity profiles obtained with statically-applied oscillating voltages at 0.7 MHz and 0.8 MHz. FIGS. 7-10 include results from two different experimental runs, R1 and R2.

Comparison of the images of particle distributions at different sweep rates relative to distributions obtained with statically applied oscillating voltages provides an indication of whether or not the sweep rate is too fast, based on whether the swept images match those obtained with statically applied oscillating voltages at the same frequency.

The data in this example shows the applicability of the disclosed methods and in particular the similarity in maximum sweep rates for various blood types. The data also shows the dependence of the maximum sweep rate on conductivity of the solution in which the particles (RBCs) are suspended.

Example 3

Conditions for Example 3 are the same as described above for Examples 1 and 2 except where otherwise stated.

One factor which may affect the maximum sweep rate is the conductivity of the solution in which the particles are suspended. Accordingly, experiments were carried out to determine the extent to which conductivity impacts the maximum sweep rate.

FIGS. 14-23 show the effect of changes in conductivity on the maximum sweep rate using red blood cells. When using biological material, and in particular cells such as red blood cells, it is important when varying the conductivity of the solution to maintain the overall tonicity of the solution within a limited range. For the experiments in FIGS. 14-23, varying combinations of NaCl and dextrose were combined to achieve the stated levels of conductivity of 0.10 S/m, 0.25 S/m, 0.50 S/m, and 1.0 S/m while maintaining the solution at approximately isotonic levels for human red blood cells; increasing the amount of NaCl increases the conductivity and proportionately less dextrose is used as NaCl is increased in order to maintain a relatively constant tonicity (see An et al. 2014, incorporated herein by reference).

Figure 14:
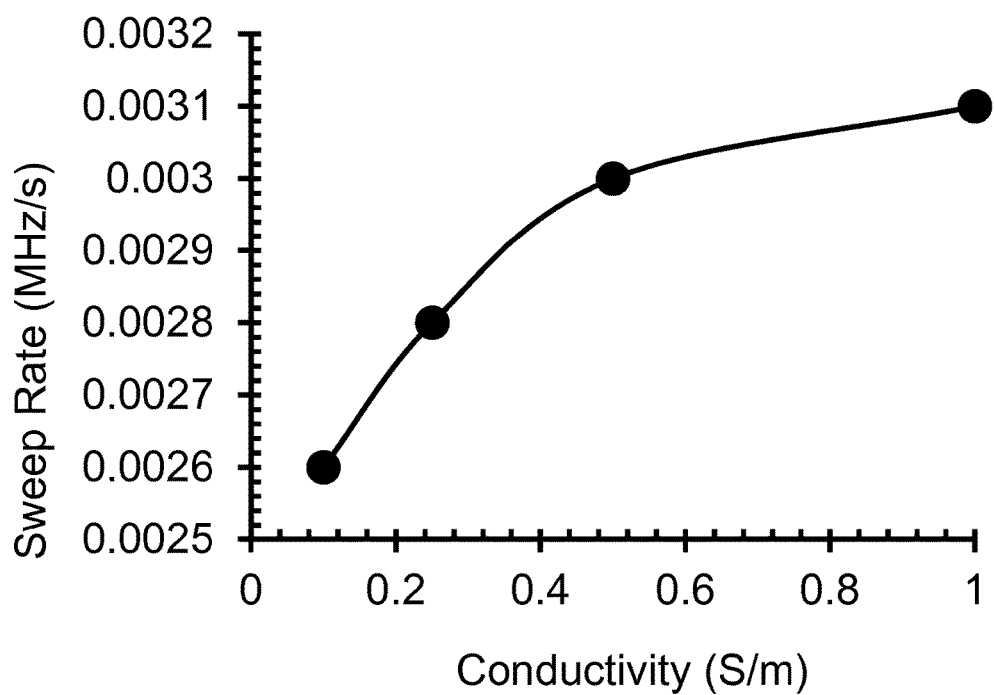
FIG. 14 shows a plot of sweep rate (MHz/s) as a function of conductivity of a solution. The plot points are a sweep rate at which the results for a given conductivity were no longer accurate. The plotted curve defines a threshold sweep rate. Thus, sweep rates above the threshold sweep rate for a given concentration are too fast, and any sweep rate below the curve may be used accurately and reliably. This aids in determining the fastest sweep rates that may be used for a solution with a given concentration in order to decrease the overall time needed for the procedure.
Figure 15:
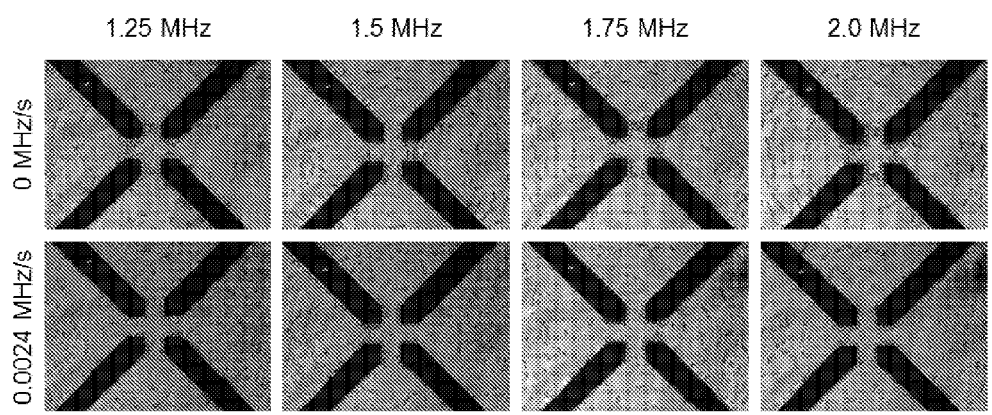
FIG. 15 shows RBC static images (top row) compared to RBCs response using 0.0024 MHz/s (bottom row). Each test was completed with A+ blood in 0.10 S/m at $1000V_{pp}$/cm. This illustrates the visual similarity between the static response and response at this sweep rate at the solution conductivity of 0.10 S/m.
Figure 16:
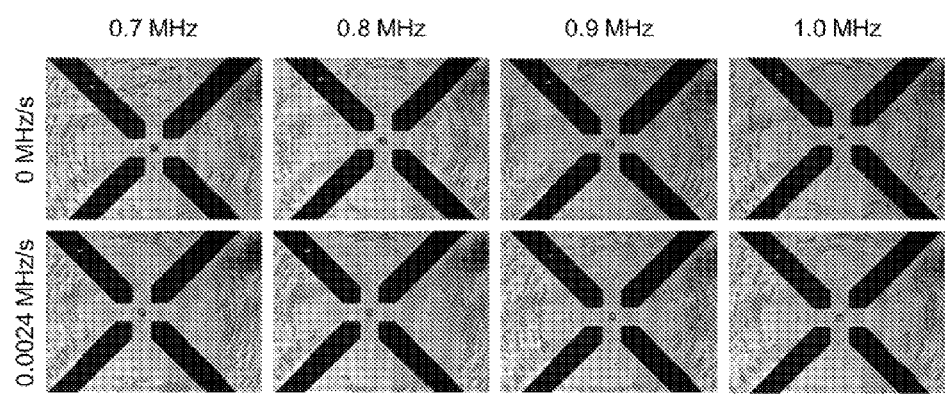
FIG. 16 shows RBC static images (top row) compared to RBCs response using 0.0024 MHz/s (bottom row). Each test was completed with A+ blood in 0.50 S/m at $1000V_{pp}$/cm. This illustrates the visual similarity between the static response and response at this sweep rate at the solution conductivity of 0.50 S/m.
Figure 17:
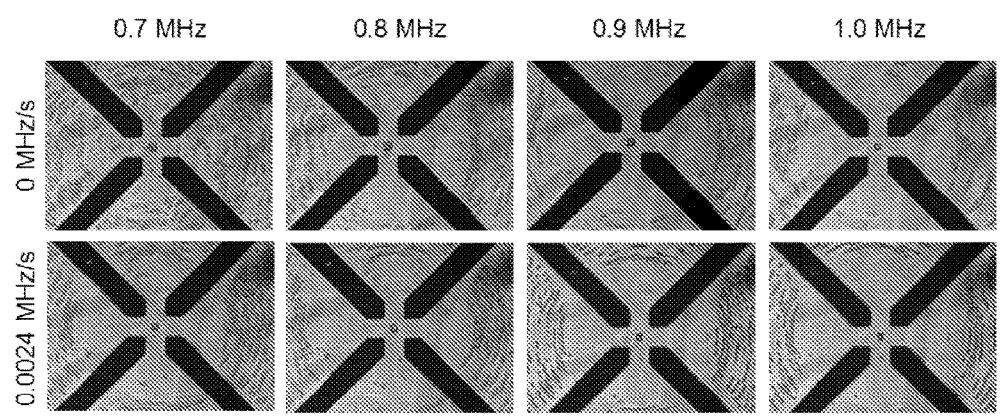
FIG. 17 shows RBC static images (top row) compared to RBCs response using 0.0024 MHz/s (bottom row). Each test was completed with A+ blood in 1.00 S/m at $1000V_{pp}$/cm. This illustrates the visual similarity between the static response and response at this sweep rate at the solution conductivity of 1.0 S/m.
Figure 18:
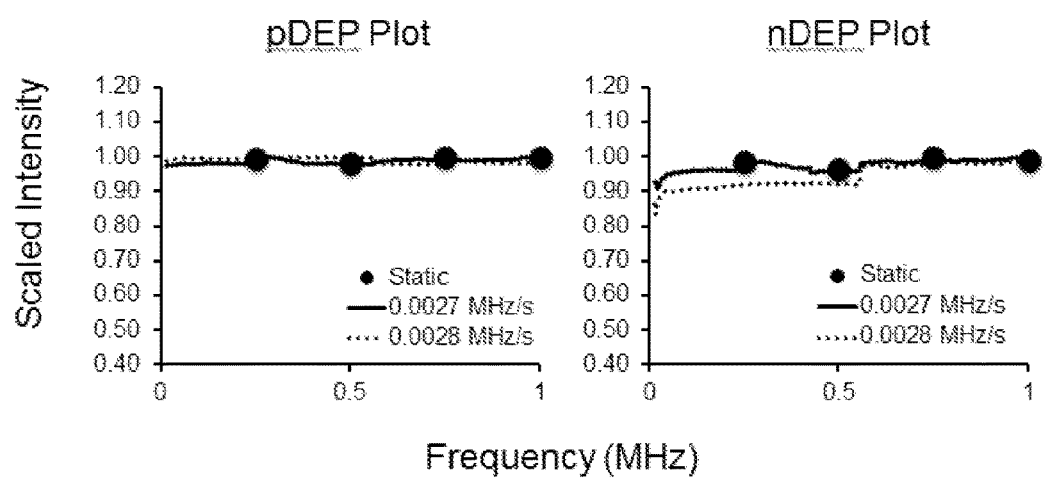
FIG. 18 shows pDEP and nDEP plots of scaled intensity versus frequency for A+ blood in 0.25 S/m at $1000V_{pp}$/cm. This plot generally shows the 0.0027 MHz/s sweep rates near the threshold sweep rate for this concentration match the static frequency data well, but the 0.0028 MHz/s sweep rate begins to falter.
Figure 19:
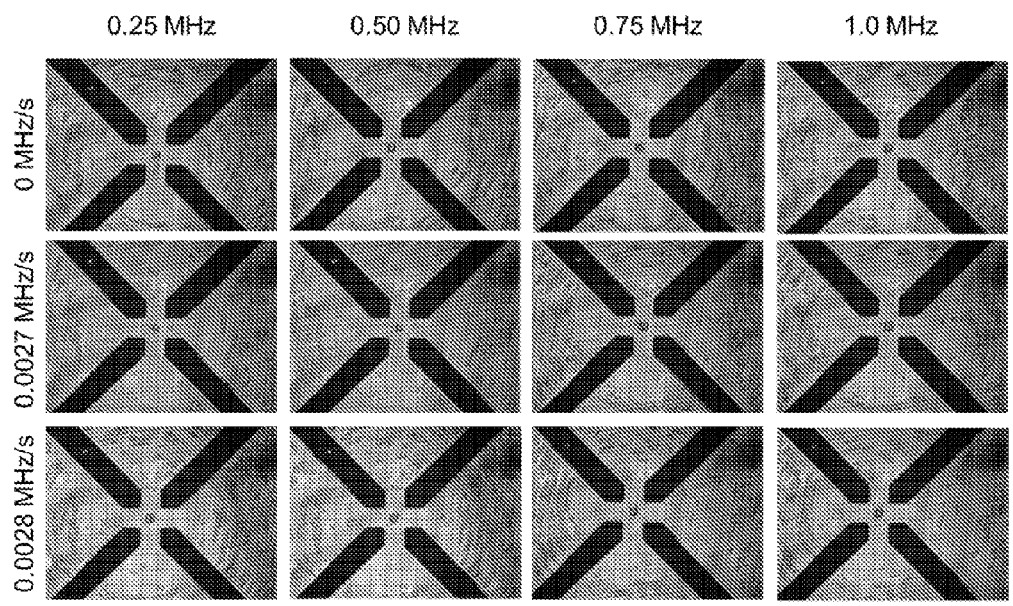
FIG. 19 shows RBC static images (top row) compared to RBCs response using 0.0027 MHz/s and 0.0028 Mhz/s (middle and bottom row). Each test was completed with A+ blood in 0.25 S/m at $1000V_{pp}$/cm. This illustrates the visual similarity between the static response and the response at a sweep rate near the threshold sweep rate for the given conductivity of the solution.
Figure 20:
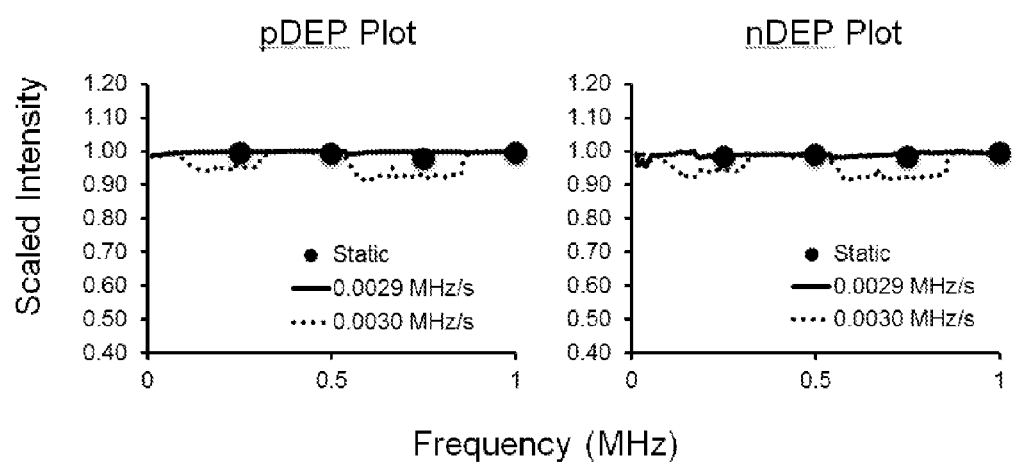
FIG. 20 shows pDEP and nDEP plots of scaled intensity versus frequency for A+ blood in 0.5 S/m at $1000V_{pp}$/cm. This plot generally shows the 0.0029 MHz/s sweep rates near the threshold sweep rate for this concentration match the static frequency data well, but the 0.0030 MHz/s sweep rate begins to falter.
Figure 21:
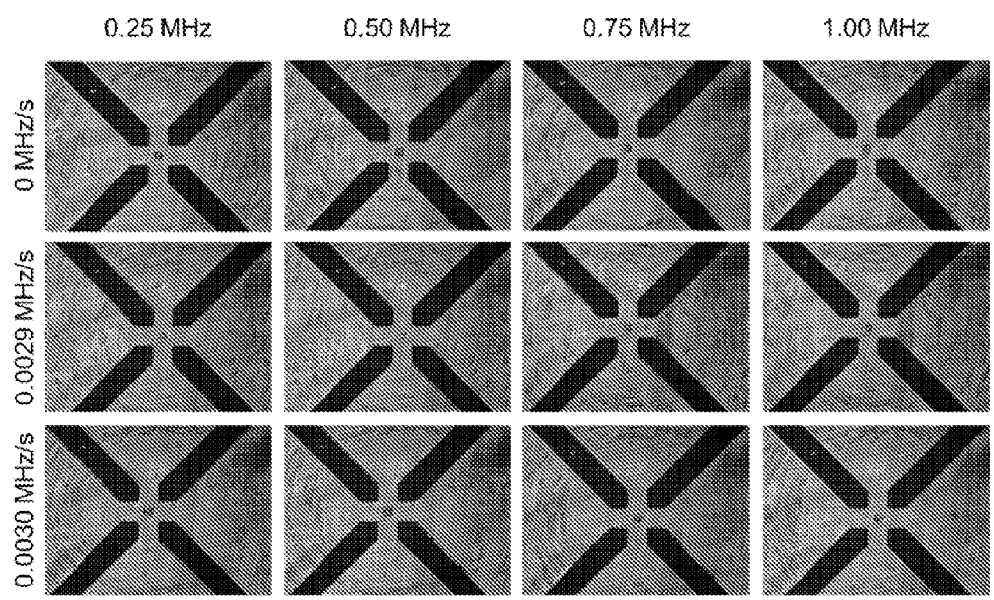
FIG. 21 shows RBC static images (top row) compared to RBCs response using 0.0029 MHz/s and 0.0030 Mhz/s (middle and bottom row). Each test was completed with A+ blood in 0.50 S/m at 1000 $V_{pp}$/cm. This illustrates the visual similarity between the static response and the response at a sweep rate near the threshold sweep rate for the given conductivity of the solution.
Figure 22:
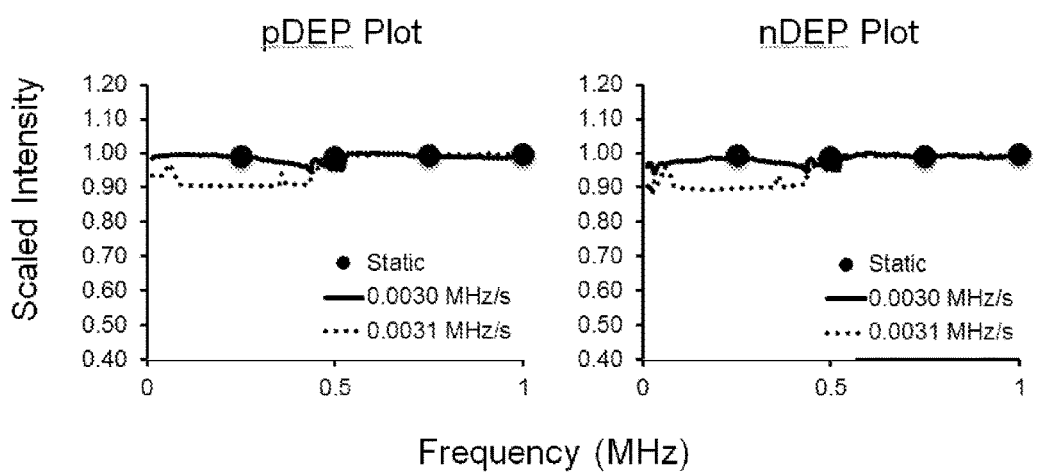
FIG. 22 shows pDEP and nDEP plots of scaled intensity versus frequency for A+ blood in 1.0 S/m at $1000V_{pp}$/cm. This plot generally shows the 0.0030 MHz/s sweep rates near the threshold sweep rate for this concentration match the static frequency data well, but the 0.0030 MHz/s sweep rate begins to falter.
Figure 23:
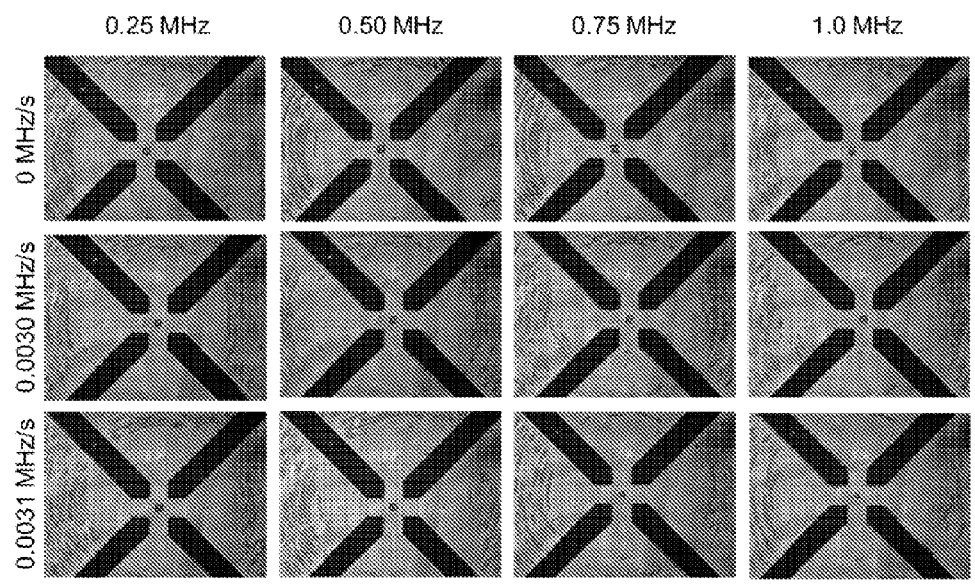
FIG. 23 shows RBC static images (top row) compared to RBCs response using 0.0030 MHz/s and 0.0031 MHz/s (middle and bottom row). Each test was completed with A+ blood in 1.00 S/m at 1000 $V_{pp}$/cm. This illustrates the visual similarity between the static response and the response at a sweep rate near the threshold sweep rate for the given conductivity of the solution.

As shown in FIG. 14, increasing conductance from 0.10 S/m to 1.0 S/m has the effect of increasing the maximum sweep rate that can be used from less than 0.0026 MHz/s at 0.1 S/m to less than 0.0031 MHz/s at 1.0 S/m. As seen in FIGS. 15-23, using a sweep rate below the maximum level generates particle distributions at various frequencies that are equivalent to distributions that are obtained with the application of an oscillating voltage at a static frequency. Increasing the conductance permits the use of a faster sweep rate, which in turn permits data to be collected at a faster rate.

Example 4

Conditions for Example 4 are the same as described above for Examples 1-3 except where otherwise stated.

The experiments of Example 4 demonstrate that particle DEP behavior is independent of the 'direction' of sweeping, i.e. sweeping the oscillating voltage signal from a high frequency to a low frequency generates equivalent results as when the oscillating voltage is swept from a low frequency to a high frequency.

Figure 24:
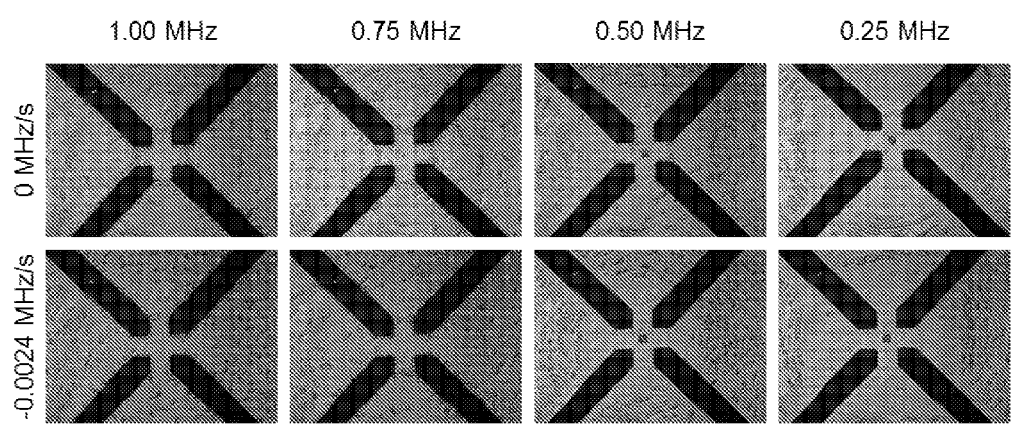
FIG. 24 shows RBC static images (top row) compared to RBCs response using a sweep rate of −0.0024 MHz/s (bottom row). Each test was completed with A+ blood in 0.10 S/m at 1000 $V_{pp}$/cm.
Figure 25:
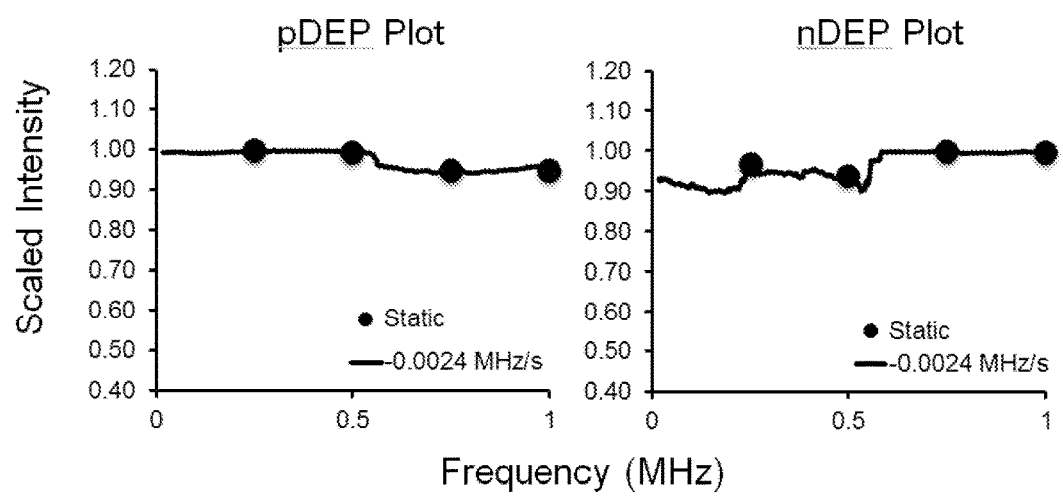
FIG. 25 shows pDEP and nDEP plots of scaled intensity versus frequency for A+ blood in 0.10 S/m at 1000 $V_{pp}$/cm using the reverse sweep method as illustrated by the images in FIG. 24.

FIG. 24 shows RBC static images (top row) compared to RBCs response using a sweep rate of −0.0024 MHz/s (bottom row). Each test was completed with A+ blood in 0.10 S/m at 1000 $V_{pp}$/cm. FIG. 25 shows pDEP and nDEP plots of scaled intensity versus frequency for A+ blood in 0.10 S/m at 1000 $V_{pp}$/cm using the reverse sweep method as illustrated by the images in FIG. 24.

Figure 26:
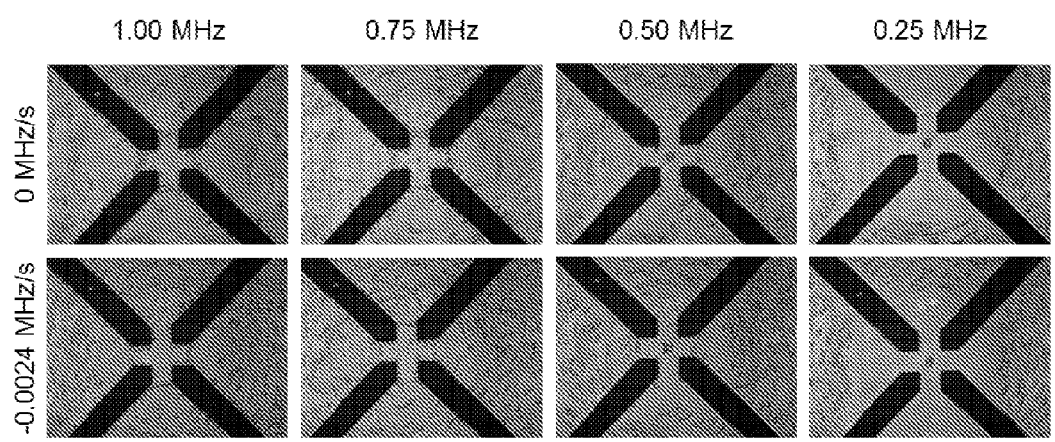
FIG. 26 shows RBC static images (top row) compared to RBCs response using 0.0024 MHz/s (bottom row). Each test was completed with A+ blood in 0.10 S/m at 1000 $V_{pp}$/cm.
Figure 27:
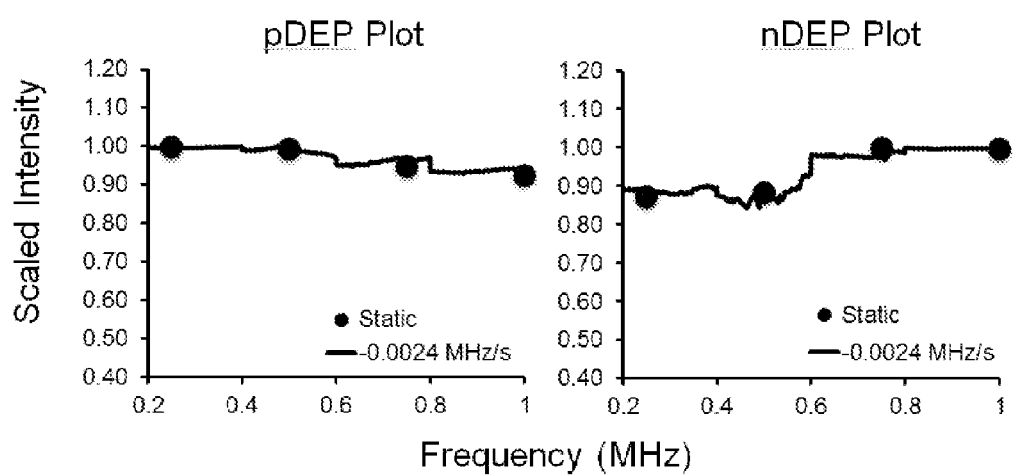
FIG. 27 shows pDEP and nDEP plots of scaled intensity versus frequency for A+ blood in 0.10 S/m at 1000 $V_{pp}$/cm using the reverse sweep method as illustrated by the images in FIG. 26.

FIG. 26 shows RBC static images (top row) compared to RBCs response using 0.0024 MHz/s (bottom row). Each test was completed with A+ blood in 0.10 S/m at 1000 $V_{pp}$/cm. FIG. 27 shows pDEP and nDEP plots of scaled intensity versus frequency for A+ blood in 0.10 S/m at 1000 $V_{pp}$/cm using the reverse sweep method as illustrated by the images in FIG. 26.

REFERENCES

Each of the following references is incorporated herein by reference in its entirety:

A. Salmanzadeh, L. Romero, H. Shaflee, R. C. Gallo-Villanueva, M. A. Stremler, S. D. Cramer and R. V. Davalos, Lab on a Chip 12, 182 (2012).
L. Rozitsky, A. Fine, D. Dado, S. Nussbaum-Ben-Shaul, S. Levenberg, G. Yossifon, Biomed Microdevices 15, 859 (2013).
R. An, D. O. Wipf, A. R. Minerick, Biomicrofluidics 8, issue 2, article 021803 (2014).
H. Xie, R. Tewari, H. Fukushima, J. Narendra, C. L. Heldt, J. King, A. Minerick, J. Vis. Exp. 88, e51696 (2014).
F. Grom, J. Kentsch, T. Muller, T. Schnelle, and M. Stelzle, Electrophoresis 27, 1386 (2006).
C. Grosse and A. V. Delgado, Current Opinion in Colloid & Interface Sciences 15, 145 (2010).
H. Morgan and N. G. Green, R. Pethig, AC Electrokinetics: colloids and nanoparticles (Research Studies Press Limited, Philadelphia, 2003).
M. Mittal, P. P. Lele, E. W. Kaler, and E. M. Furst, Journal of Chemical Physics 129, 065413 (2008).
K. Ogata, System Dynamics (Prentice-Hall Inc, Englewood Cliffs, 1978).
P. Gascoyne, J. Satayavivad, and M. Ruchirawat, Acta Tropica 89, 357 (2004)

Various features of the invention are set forth in the following claims.

What is claimed is:

1. A method of identifying a particle, comprising the steps of:
receiving a plurality of particles adjacent a microelectrode array, the microelectrode array comprising a plurality of electrodes, the microelectrode array including a first plurality of electrodes to provide a first charge and a second plurality of electrodes to provide a second charge, the second charge being different than the first charge, and the second plurality of electrodes being in a nonparallel relationship with the first plurality of electrodes;
applying an oscillating voltage signal to the microelectrode array at a plurality of frequency levels varying between a low frequency and a high frequency, the plurality of frequency levels being applied at a sweep rate, wherein the sweep rate is no more than a maximum sweep rate and is no less than a minimum sweep rate, the application of the oscillating voltage signal to the microelectrode array resulting in a spatially non-uniform field; and
determining a distribution of the plurality of particles relative to the microelectrode array at the plurality of frequency levels between the low frequency and the high frequency.

2. The method of claim 1, wherein the plurality of particles is suspended in a solution having a conductivity and wherein the maximum sweep rate is a function of the conductivity.

3. The method of claim 2, wherein the conductivity is 1.0 S/m and the maximum sweep rate is less than 0.0031 MHz/s.

4. The method of claim 1, wherein the low frequency is 0.01 MHz and the high frequency is 2.0 MHz.

5. The method of claim 1, wherein the microelectrode array is disposed within a microfluidic device.

6. The method of claim 1, wherein determining a distribution of the plurality of particles relative to the microelectrode array further comprises determining a spatial distribution of the plurality of particles relative to the microelectrode array using an image detector and an image analysis system.

7. The method of claim 6, further comprising, at each of the plurality of frequency levels, collecting an image of the microelectrode array using the image detector and determining a spatially resolvable concentration of the plurality of particles relative to the microelectrode array using the image analysis system.

8. The method of claim 7, further comprising, at each of the plurality of frequency levels, using the image analysis system to determine a first spatial distribution of the plurality of particles at a first location and a second spatial distribution of the plurality of particles at a second location.

9. The method of claim 8, wherein determining a first spatial distribution of the plurality of particles further comprises using the image analysis system to determine an intensity of the plurality of particles at the first location.

10. The method of claim 9, wherein determining a second spatial distribution of the plurality of particles at a second location further comprises using the image analysis system to determine an intensity of the plurality of particles at the second location.

11. The method of claim 10, further comprising comparing the first distribution of the plurality of particles and the second distribution of the plurality of particles at the plurality of frequency levels to identify the particle.

12. The method of claim 1, wherein the plurality of particles comprises red blood cells.

* * * * *